United States Patent
Yao et al.

(10) Patent No.: US 10,653,784 B2
(45) Date of Patent: May 19, 2020

(54) HYDROPHOBIC HIGHLY BRANCHED CARBOHYDRATE POLYMERS

(71) Applicant: Purdue Research Foundation, West Lafayette, IN (US)

(72) Inventors: Yuan Yao, West Lafayette, IN (US); Jingmin Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/764,624

(22) PCT Filed: Oct. 3, 2016

(86) PCT No.: PCT/US2016/055180
§ 371 (c)(1),
(2) Date: Mar. 29, 2018

(87) PCT Pub. No.: WO2017/059433
PCT Pub. Date: Apr. 6, 2017

(65) Prior Publication Data
US 2018/0289815 A1 Oct. 11, 2018

Related U.S. Application Data

(60) Provisional application No. 62/236,372, filed on Oct. 2, 2015.

(51) Int. Cl.
| | | |
|---|---|---|
| A61K 47/36 | (2006.01) |
| A61K 31/12 | (2006.01) |
| A61K 31/167 | (2006.01) |
| C08B 37/00 | (2006.01) |
| C08B 3/24 | (2006.01) |
| A61K 9/10 | (2006.01) |
| A61K 47/40 | (2006.01) |
| A61K 9/16 | (2006.01) |
| A61K 9/51 | (2006.01) |
| A61K 47/38 | (2006.01) |
| A61K 31/337 | (2006.01) |
| A61K 31/343 | (2006.01) |
| A61K 31/496 | (2006.01) |
| A61K 31/635 | (2006.01) |
| C08J 3/24 | (2006.01) |

(52) U.S. Cl.
CPC ............... *A61K 47/36* (2013.01); *A61K 9/10* (2013.01); *A61K 9/1676* (2013.01); *A61K 9/1682* (2013.01); *A61K 9/5161* (2013.01); *A61K 31/12* (2013.01); *A61K 31/167* (2013.01); *A61K 31/337* (2013.01); *A61K 31/343* (2013.01); *A61K 31/496* (2013.01); *A61K 31/635* (2013.01); *A61K 47/38* (2013.01); *A61K 47/40* (2013.01); *C08B 37/0009* (2013.01); *C08J 3/24* (2013.01); *C08J 2305/00* (2013.01)

(58) Field of Classification Search
CPC .... A61K 47/36; A61K 31/167; A61K 31/343; A61K 31/496; A61K 31/12; A61K 31/635; A61K 31/337; C08B 37/0009; C08J 3/24; C08J 2305/00
USPC ....................................... 424/70.12; 536/111
See application file for complete search history.

(56) References Cited

U.S. PATENT DOCUMENTS

| | | | | |
|---|---|---|---|---|
| 5,639,865 A | * | 6/1997 | Kalbe | C08B 13/00 428/413 |
| 2003/0031715 A1 | | 2/2003 | Park et al. | |
| 2007/0244296 A1 | | 10/2007 | Tomalia et al. | |
| 2014/0066363 A1 | | 3/2014 | Bhunia et al. | |
| 2015/0080220 A1 | | 3/2015 | Yao et al. | |

OTHER PUBLICATIONS

Rinaudo et al. Polysaccharide Derivatives. Natural Polymers and Agrofibers Composites. (ed) E. Frollini. A.L. Leao and L.H.C. Mattoso. Sao Carlos—Brazil—2000. pp. 15-39. (Year: 2000).*

* cited by examiner

*Primary Examiner* — Yih-Horng Shiao
(74) *Attorney, Agent, or Firm* — Purdue Research Foundation; Liang Zeng Yan

(57) ABSTRACT

A material comprising a highly branched carbohydrate polymer, a polyalkylene glycol (or polyalkylene oxide) linked to the highly branched carbohydrate polymer, and a hydrophobic or amphiphilic group linked to the highly branched carbohydrate polymer and/or the polyalkylene glycol (or polyalkylene oxide), is described. Methods of making and using the material, as well as a soluble composition that contains the material and a hydrophobic solute compound, are also described.

7 Claims, 12 Drawing Sheets

NATIVE PHYTOGLYCOGEN

HYDROXYPROPYL GROUPS

OCTENYL SUCCINATE GROUPS

GRAFTED OCTENYL SUCCINATE HYDROXYPROPYL GROUPS

MOLECULES OF ACTIVE PHARMACEUTICAL INGREDIENT (API)

HYDROPHOBIC HIGHLY BRANCHED CARBOHYDRATE POLYMERS

CROSS-REFERENCE TO RELATED APPLICATIONS

The present U.S. patent application is a 35 U.S.C. § 371 national phase application of PCT/US/2016/055180, filed Oct. 3, 2016, which is related to and claims the benefit of U.S. Provisional Application Ser. No. 62/236,372, filed on Oct. 2, 2015, the disclosure of which is hereby incorporated by reference in its entirety.

GOVERNMENT FUNDING

This invention was made with Government support under IIP1346431 and DMR1310475 awarded by the National Science Foundation. The Government has certain rights in the invention.

TECHNICAL FIELD

The present disclosure relates generally to compositions for increasing the solubility and stability of solute compounds therein, and more particularly to compositions including highly branched carbohydrate polymers or polysaccharides (hereafter, highly branched carbohydrate polymers or polysaccharides indicate their original forms or modified forms), solubilizing agents that may be used to improve solubility, stability, and/or bioavailability of solute compounds for the food, nutraceutical, personal care, skin care, cosmetics, pharmaceuticals, medical, paint and coating, and agricultural industries.

BACKGROUND

In industries such as food, feed, agriculture, drug, animal drug, personal care, skin care, etc., the use of certain ingredients or extracts is difficult since their constituent materials have low or poor solubility in water, which leads to low stability, accessibility, availability, or bioavailability. Examples of such ingredients, synthetic compounds, or extracts can include phenolic compounds (e.g., flavonoids, curcuminoids), carotenoids, and active pharmaceutical ingredients (APIs, e.g., drugs), as well as raw or purified extracts from herbs, microbes and animals.

For drugs administered via oral route, drugs must be dissolved for the molecules to permeate through cell membranes to reach the systemic circulation. The solubility and permeability of drug are largely affected by their physicochemical properties. In addition to neutral drugs (e.g. griseofulvin), a large number of drug compounds are either weak acids (e.g. ibuprofen) or bases (e.g. itraconazole). For these drugs, their un-ionized and ionized forms in water affect their solubility and permeability. Along the GI tract, the small intestine provides the largest surface area for drug absorption, and its membranes are more permeable than those in the stomach. In general, the intestinal pH (5-7) affects the solubility of drugs and their membrane permeability. For weak acids, their solubility is improved due to ionization; for weak bases, their solubility is reduced due to un-ionization.

It is estimated that roughly 40% of new drug molecules present drug delivery challenges due to their low solubility. The Biopharmaceutics Classification System (BCS) was developed as a systematic approach to classify Active Pharmaceutical Ingredients (APIs) based on their solubility and permeability. Based on the BCS, drug solubilization is necessary for the delivery of compounds in Class II (low solubility, high permeability) and Class IV (low solubility, low permeability). In particular, compounds in Class II, such as griseofulvin, make the group for which the solubilization technologies can readily solve the drug delivery problem.

Accordingly, there are different approaches for addressing the solubility issue of active ingredients (AIs), such as nanoemulsions, dendrimers, block copolymer micelles, cocrystal formation, and amorphous dispersions. The amorphous dispersion approach has drawn great interest in drug formulation due to several reasons. First, it has the potential to eliminate the solubility limitations imposed by the thermodynamic stability of crystal lattice. Second, by the action of polymer matrix it is possible to induce supersaturation over time scales comparable to those required for systemic absorption.

One particular example of such ingredients or extracts includes phenolic compounds, such as quercetin and curcumin. Quercetin and curcumin are strong antioxidants and have anti-inflammatory, antiviral, and anti-cancer effects. In particular, curcumin is a potent anti-cancer drug that can be used clinically. However, their low solubility prohibits their use in food, nutraceutical, cosmetic, and medical formulations. To address this problem, a variety of techniques have been employed to improve the water-solubility of such low or non-soluble phenolic compounds. For example, it has been proposed to improve the solubility or bioavailability of curcumin using specific compounds (e.g., piperine), polymeric nanoparticle encapsulation, or surfactant micelles. However, these methods are expensive and/or have limited capability to solubilize phenolic compounds. In addition, some of these strategies are simply ineffective.

Poor water solubility of some active pharmaceutical ingredients (APIs), such as a number of drugs is one of the major problems in drug formulation and drug absorption. Systems to improve the water solubility of these drugs are essential for their bioavailability. For example, application of paclitaxel in cancer therapy has been limited by its low water solubility, and current practice of dissolving paclitaxel usually leads to short-term physical stability with quick precipitation of drug molecules. To enhance paclitaxel solubility and physical stability, solvents have been used to disperse drug molecules. To be effective, however, the concentration of solvents needs to be very high, which may lead to difficulties in formulation and administration.

Another example is ibuprofen. Ibuprofen is a nonsteroidal anti-inflammatory drug (NSAID), and a core medicine in the WHO Model List of Essential Medicines. It is broadly used to relieve symptoms of arthritis and fever and as an analgesic where there is an inflammatory component and dysmenorrhea. Ibuprofen belongs to Biopharmaceutics Classification System (BCS) class II, for which the rate of drug dissolution or drug solubility is the rate-limiting step in the absorption.

Another example is griseofulvin. Griseofulvin is a widely used antifungal drug in the treatment of mycotic diseases of skin, hair and nails. Griseofulvin is poorly soluble in water and has been used as a standard in the research to increase drug bioavailability.

Another example is itraconazole. Itraconazole is an orally active triazole antimycotic agent and has been used to treat various fungal infections including histoplasmosis, blastomycosis and oncomycosis. It is a weakly base drug with poor water solubility.

Other examples are aripiprazole, celecoxib, imatinib, ezetimibe, modafinil, dutasteride, ciclosporin, darunavir, raloxifene, olmesartan, and cinacalcet. Their low solubility affects their efficacy at various levels.

Similar issues persist in industries related to the extraction and formulation of medicinal, nutritional, or functional materials from plant, microbial, or animal organisms, such as herbal extracts, Chinese medicine, and colorants. In such industries, there are a number of extraction processes, including: (1) aqueous extraction; (2) solvent-based extraction, and (3) supercritical fluid extraction. In many circumstances, the solute compound (or materials) has low water solubility, which makes it difficult to formulate as a product. Additionally, in industries related to feed, animal drugs, personal care, cosmetics, paints, pesticides, herbicides, or other food and non-food areas, the low solubility of certain materials in products is the source of numerous difficulties in formulation, processing and/or the function of such products.

SUMMARY

Compositions for increasing the solubility and stability of solute compounds are described herein. More particularly, the inventors have surprisingly discovered that highly branched carbohydrate polymers, such as alpha-D-glucans, when subjected to two steps of substitution, for which the first step was reaction with a polyalkylene glycol or polyalkylene oxide-forming agents (e.g., alkylene oxides) and the second step was with hydrophobic or amphiphilic groups, may have high capability to increase the solubility of poorly water-soluble compounds, including active pharmaceutical ingredients, hydrophobic nutrients, as well as other types of compounds with low water solubility. Thus these modified highly branched carbohydrate polymers can be used as solubilizing agents. In the present invention, a solubilizing agent is a compound, molecule, material, substance, mixture, or composition that is able to improve the solubility, dissolution rate, and/or stability in solution of a hydrophobic solute compound.

The highly branched carbohydrate polymer can be highly branched alpha-D-glucans such as glycogen, phytoglycogen, amylopectin, dextran, maltodextrins, dextrins, and other branched glucans naturally occurring, modified natural glucans, or artificially synthesized branched materials such as those made from glucan chains using starch branching enzyme, glucan branching enzyme, or their functional analogs.

The highly branched carbohydrate polymer can also be non-glucan, but highly branched materials, such as gum Arabic and its derivatives, and arabinoxylan and its derivatives. In other embodiments, the highly branched carbohydrate polymer is a synthesized branched material such as polydextrose and its derivatives.

The highly branched carbohydrate polymer can also be a material that is a "hybrid," for example, the material formed through covalent connections between two types of polysaccharide, between a polysaccharide and a protein (or a lipid), or between a polysaccharides and a monosaccharide or a oligosaccharide.

BRIEF DESCRIPTION OF THE FIGURES

The present invention may be more readily understood by reference to the following drawings, wherein.

supernatant from centrifuged dispersion of pure niclosamide in HBSS at dispersing dose of 1000 and 100 µg/mL, respectively. Cel-1000 and Cel-100: supernatant from centrifuged dispersion of pure celecoxib in HBSS at dispersing dose of 1000 and 100 µg/mL, respectively. Nic-OHPP-100: supernatant from centrifuged dispersion of Nic-OHPP in HBSS at dispersing dose of 100 µg/mL (for pure niclosamide). Cel-OHPP-HPMCAS-100: supernatant of Cel-OHPP-HPMCAS dispersed in HBSS buffer at 100 µg/mL.

Figure 11A:
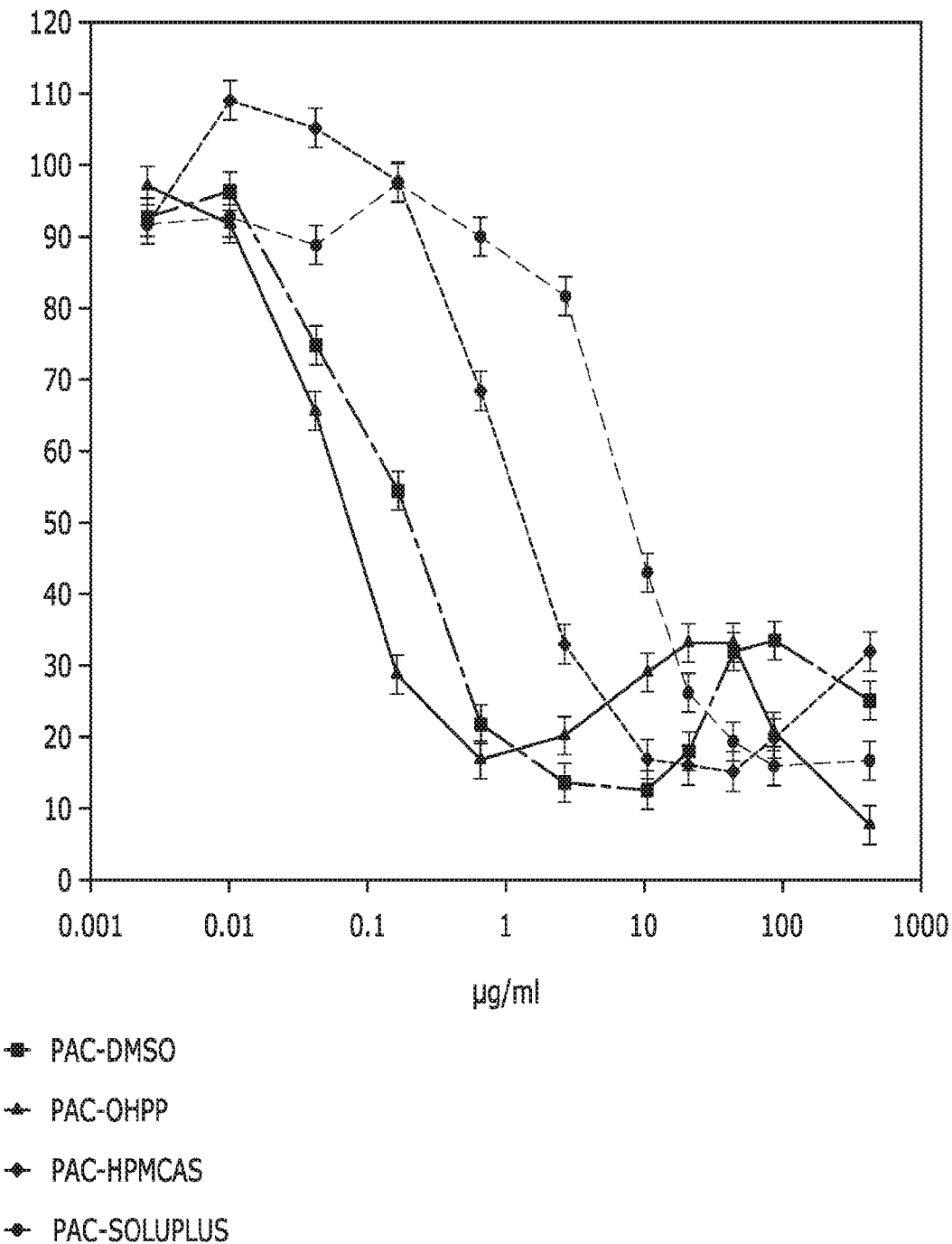
Figure 11B:
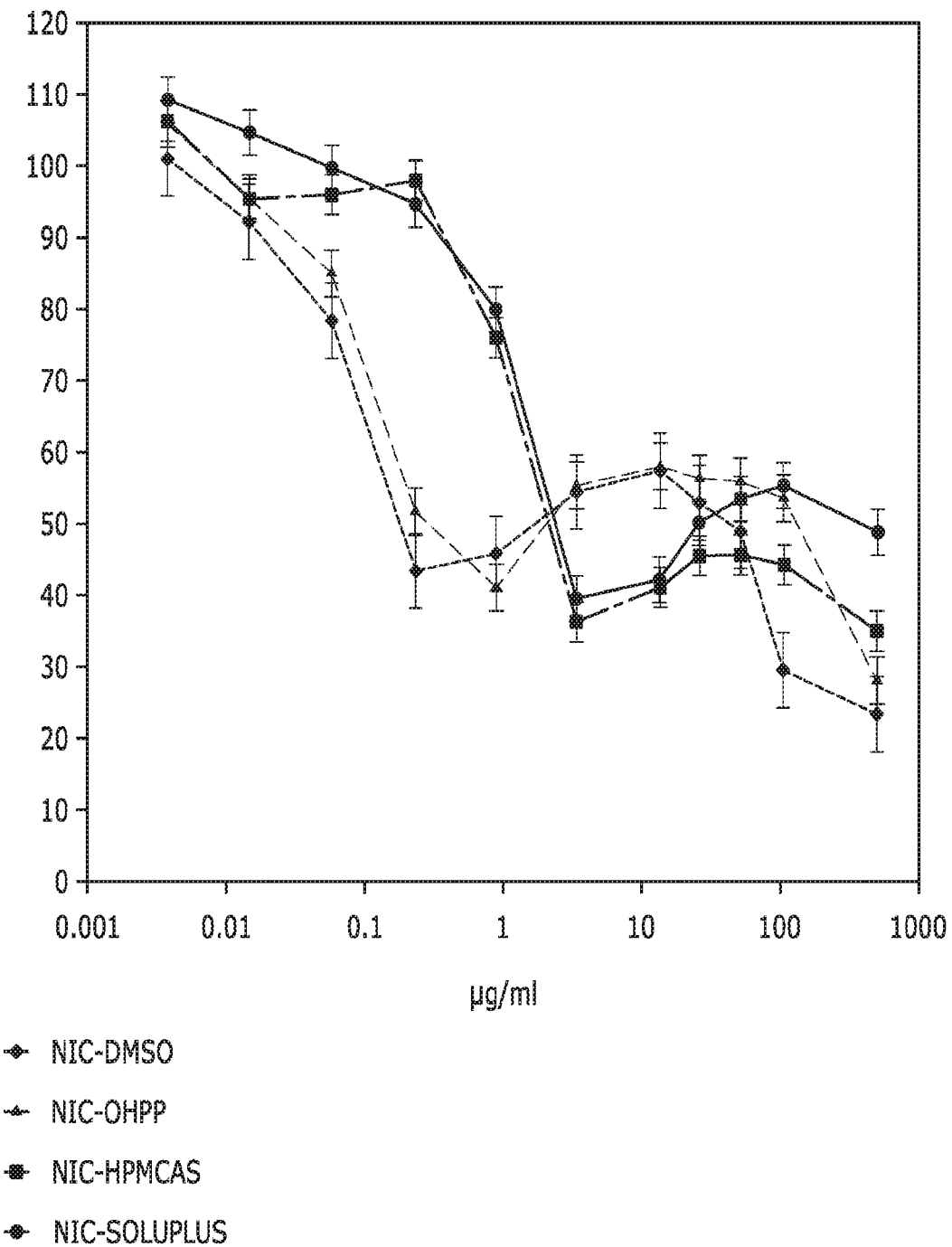

FIGS. 11A and 11B provide graphs showing the MTT cell viabilities of (A) HeLa cells after a 48 h-exposure to paclitaxel and (B) PC-3 cells after a 48 h-exposure to niclosamide, as affected by the apparent doses of APIs delivered using various types of excipient (DMSO, OHPP, HPMCAS, and Soluplus). For Pac-DMSO and Nic-DMSO, the testing preparation was made through dissolving the API with DMSO and then diluting the solution to 0.003 to 500 µg/mL. For API-excipient preparations, each individual API-excipient complex (in solid form) was first mixed in cell culture medium to achieve a total API amount of 2.5 mg/mL, and then the mixture was centrifuged at 16,000 g for 5 min. The supernatant thus collected, which was deemed as having an apparent API dose of 2.5 mg/mL, was diluted 5 to 819,200 times to achieve a group of apparent API doses ranging from 0.003 to 500 µg/mL.

DETAILED DESCRIPTION

An aqueous solution, as used herein, is any solution in which water is the main solvent. The aqueous solution can include other solvents, and one or more additional solutes, while still remaining an aqueous solution. Examples of aqueous solutions include buffered solutions, salt water, drinks such as coffee, tea, beer, wine, and fruit juice, vinegar, etc. An aqueous solution can also be a phase of an emulsion (e.g. cream, lotion), a colloid, a suspension, or aerosol.

Solubility, as used herein, refers to the ability of a solute compound to dissolve or disperse in a liquid solvent to form a homogeneous solution or dispersion of the solute in the solvent.

Practically, the term "solubility" indicates the amount of solute in a given solvent that remains stable in a dispersed state over a defined or desirable period of time, against various forms of precipitation, sedimentation, aggregation, flocculation, gelation, coacervation, creaming, agglomeration, coalescence, or phase separation. Technically, the solubility defined here can be measured using a centrifugation, a filtration, or an ultrafiltration approach. For example, for a centrifugation approach, the mixture of solute and liquid solvent is subjected to centrifugation and the amount of solute in the supernatant is determined to calculate the solubility. For an ultrafiltration approach, the mixture of solute and liquid solvent is subjected to ultrafiltration and the amount of solute in the permeated fluid is determined to calculate the solubility.

The solubility of a solute compound can vary depending on a number of factors, such as the temperature, pressure, ionic strength, types of buffer, presence of other solute(s) in the solvent, and the pH value of the solution. Increased solubility, as used herein, refers to the ability for an increased amount of a solute to dissolve or disperse in an aqueous solution of a given composition at a given set of conditions and remain stable. The extent of the solubility of a substance in a specific solvent is measured as the kinetically stable concentration under a defined set of measuring conditions. Therefore, adding more solute may or may not increase the concentration of the solute in the solution or dispersion. Solubility is commonly expressed as a concentration.

Solubilizing Agent

A solubilizing agent is a compound, molecule, material, substance, mixture, or composition that is able to improve the solubility, dissolution rate, and/or stability in solution of a hydrophobic solute compound. In particular, the solubility of a solute compound in presence of a solubilizing agent is higher than the solubility of the solute compound in absence of a solubilizing agent.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

"Pharmaceutically acceptable" as used herein means that the compound or composition is suitable for administration to a subject to achieve the treatments described herein, without unduly deleterious side effects in light of the severity of the disease and necessity of the treatment.

Preparation of Hydrophobically Modified Phytoglycogen or Glycogen-Type Materials The inventors have developed a number of chemically modified highly branched carbohydrate polymer prototypes. Some examples are: octenylsuccinate hydroxyethyl phytoglycogen (OHEP), octenylsuccinate hydroxypropyl phytoglycogen (OHPP), octenylsuccinate hydroxypropyl phytoglycogen beta-dextrin (OHPPB), propionate hydroxypropyl phytoglycogen (PHPP), acetate hydroxypropyl phytoglycogen (AHPP), and propionate octenylsuccinate hydroxypropyl phytoglycogen (POHPP). These new materials are defined herein as "hydrophobically modified phytoglycogen or glycogen-type (HMPGT)" materials. HMPGT materials belong to the broader class of hydrophobic highly branched carbohydrate polymers.

The name of each HMPGT is not binding due to the multiple approaches with nomenclature. For example, octenylsuccinate hydroxypropyl phytoglycogen (OHPP) can also be named as octenylsuccinate polypropylene glycol phytoglycogen (OPPGP) or octenylsuccinate polypropylene oxide phytoglycogen (OPPOP). The general chemical nature of each HMPGT material is defined by the approach in preparing them. Phytoglycogen or glycogen-type (PGT) materials are used as the starting material for substitutions, grafting, or conjugating. The PGT materials include: glycogen, phytoglycogen, glycogen-type materials extracted from microbiological, plant, or animal resources, and highly branched biopolymers synthesized through genetic, chemical, physical, and enzymatic approaches. For example, highly branched glucan molecules synthesized by using starch branching enzymes belong to PGT materials defined herein.

To the molecule of a PGT material, the first-step substitution (modification) is conducted using a polyalkylene glycol, alkylene oxide, or their combinations. This first-step substitution can also be conducted using chains of polyethylene glycol, polypropylene glycol, their mixtures, or their co-polymers. In addition, the first-step substitution can be conducted using other types of polymers. One structural outcome of this first-step substitution is to form an accumulation of linear or branched chains at the surface of PGT particulates. The accumulation of these chains may form a layer at the surface of PGT particulates, or may form other types of distribution pattern with PGT materials. For example, the substitution may occur at both the external and internal regions of PGT particulates, and the distribution can be even or uneven based on the protocols used for this first-step substitution reaction.

After the first-step substitution, the second-step substitution (modification) is conducted to bring hydrophobic, lipophilic, or amphiphilic moieties to the PGT-based particulates. One purpose of this second-step substitution is to promote the interactions between the PGT-based particulates and the hydrophobic compounds, such as APIs (active pharmaceutical ingredients). Accordingly, in this second material. For example, if 5 mol of hydroxypropyl groups (one hydroxypropyl group being generated from one propylene oxide) are attached to a certain amount of PGT material that contains 10 mol of glucosidic units, then DS is calculated as: DS=(5 mol)/(10 mol)=0.5. The DS value can be determined by various methods, such as titration, NMR, HPLC, MS, colorimetric methods, and others. Preferably, the first-step substitution DS is between 0.01 and 10,000.

The second-step (Step-2) substitution can be carried out using various methods, such as reacting the PGT-based materials with an anhydride (e.g. octenyl succinic anhydride, acetic anhydride, propionic anhydride). For the second-step substitution, the degree of substitution (DS) is defined as the molar ratio between the attached hydrophobic, lipophilic, or amphiphilic groups and the total glucosyl units of the PGT-based material. The DS value can be determined by various methods, such as titration, NMR, HPLC, MS, colorimetric methods, and others. In this invention, the second-step substitution DS is between 0.01 and 10.

The reaction scheme of preparing octenylsuccinate hydroxypropyl phytoglycogen (OHPP) is described in Scheme 1.

Scheme 1: Preparation and chemical structure of octenylsuccinate hydroxypropyl phytoglycogen. "PG—OH" in the scheme indicates a hydroxyl group of phytoglycogen (PG) or its derivative.

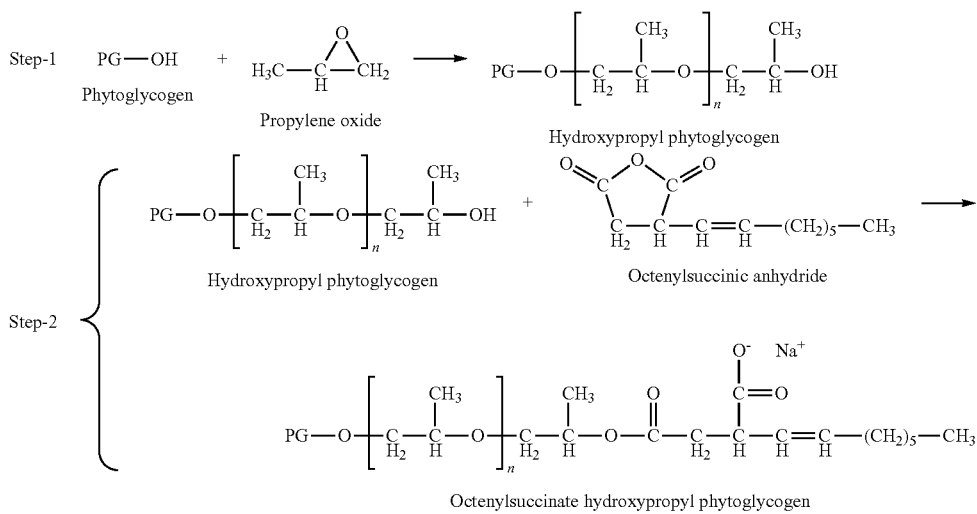

step, the modified highly branched carbohydrate formed after the first step (Step-1) is reacted with a hydrophobic or amphiphilic group to provide a solubilizing agent. The second-step substitution can be substitutions by octenylsuccinate, acetate, propionate groups, or their combinations, as well as the substitutions of other hydrophobic, lipophilic, or amphiphilic groups. In some embodiments, the hydrophobic or amphiphilic groups of the second step react with the polyalkylene glycol attached to the PGT. Alternately, or in addition, the hydrophobic or amphiphilic groups of the second step react directly with the PGT itself.

The first-step (Step-1) substitution (modification) can be carried out through a polymerization reaction using alkylene oxide monomers (such as ethylene oxide or propylene oxide) or through a grafting reaction such as PEGylation (i.e. grafting a chain segment of polyethylene glycol). The degree of substitution (DS) of the first-step substitution is defined as the molar ratio between the monomers attaching to the particulates and the total glucosyl units of PGT As shown in Scheme 1, OHPP can be prepared using two steps of reaction. In Step-1, phytoglycogen is activated using sodium hydroxide and reacted with propylene oxide to form hydroxypropyl phytoglycogen. In step-2, hydroxypropyl phytoglycogen is further reacted with octenylsuccinic anhydride under alkaline conditions to form octenylsuccinate hydroxypropyl phytoglycogen (OHPP). The OHPP material is then purified and dried to yield solid. Where Scheme 1 shows that the octenylsuccinate group attaches to the hydroxypropyl group, this does not exclude the possibility that the octenylsuccinate group may also attached directly to phytoglycogen.

Use of HMPGT Materials to Solubilize Hydrophobic Solute Compounds

The primary usage of HMPGT materials, as a fundamentally novel group of biomaterials, is to enhance the water-solubility of hydrophobic solute compounds, such as poorly water-soluble active pharmaceutical ingredients (APIs) or drug substances. For example, HMPGT may significantly enhance the water solubility or dispersity of BCS Class II and BCS Class IV drug substances. HMPGT materials are acting as solubilizing agents. As defined earlier, a solubilizing agent can increase the solubility of a solute compound.

BCS means Biopharmaceutics Classification System. According to BCS, drug substances or APIs can be classified in 4 classes:

Class I: high permeability, high solubility
Class II: high permeability, low solubility
Class III: low permeability, high solubility
Class IV: low permeability, low solubility.

As used herein, the term "solubility" indicates the capability of a solute compound, such as API compounds or drug substances to form stable, transparent or opaque dispersion in an aqueous system. "Enhanced stability" can be associated with one or multiple situations listed below:
1. Increased concentration of the solute compound, such as APIs or other substances in aqueous systems through increased equilibrium solubility.
2. Increased dissolution rate.
3. Formation of more stable supersaturated solution.
4. Formation of more stable colloidal systems, such as micellar dispersions or emulsions showing reduced phase separation, precipitation, or creaming over a relevant period of time related to processing, storage, or consumption.
5. Enhanced portion of particulates (in aqueous systems) that are smaller than a defined size, such as 50, 100, or 500 nanometers.

For a solute compound, such as API or drug substances, as a result of providing enhanced solubility, one or more of the beneficial outcomes listed below may be provided:
1. Increased bioavailability of API or drug substances
2. Increased bioaccessibility of API or drug substances
3. Increased permeation of API or drug substances
4. More convenient handling of dosage forms
5. More convenient formulations
6. Increased safety of drugs
7. Reduced cost for producing and using formulations The HMPGT and hydrophobic solute compound (e.g., API) can be incorporated using any approach that is feasible, such as extrusion, solvent (including water)-based spray drying, vacuum drying, kneading, milling, blending, and/or other types of mixing or incorporation procedures. The mixture of HMPGT and API can be in the form of powder, granulated, solid, liquid, semi-liquid, gel, film, etc. that is desirable for appropriate formulations or dosage forms.

Figure 1:
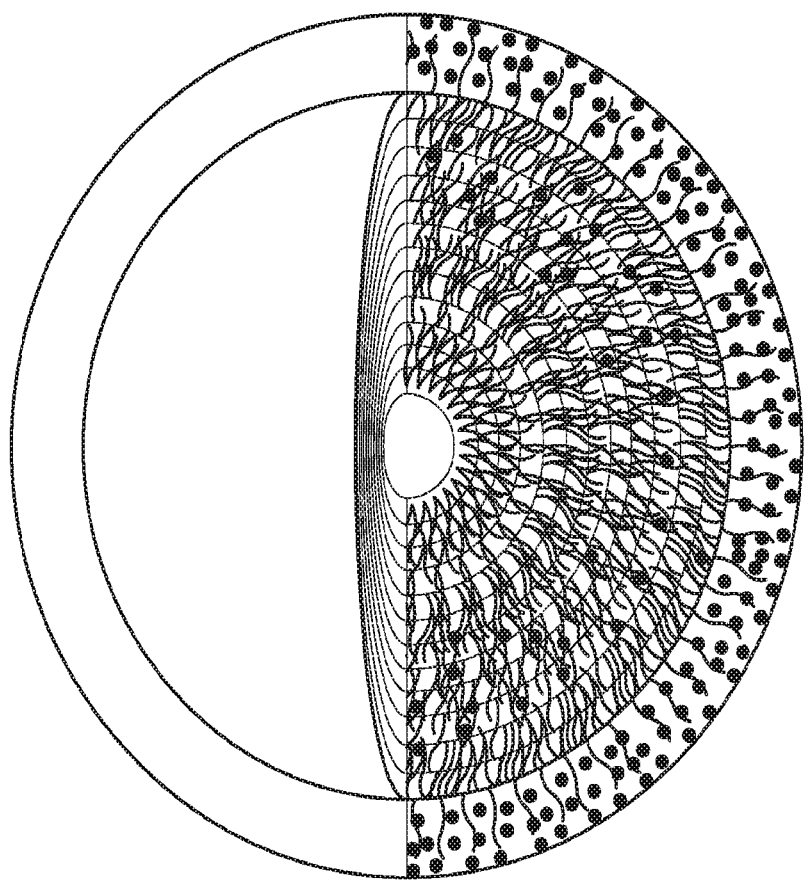
FIG. 1 provides a hypothesized (non-binding) cut-away diagram of an octenylsuccinate hydroxypropyl phytoglycogen (OHPP) nanoparticle that hosts multiple API molecules. The hydroxypropyl (HP) groups perform as "bridging units" that provide the flexibility of OS groups to interact with API molecules. The octenylsuccinate hydroxypropyl (OHP) layer (or layers) may stabilize dispersed API.
Figure 1:
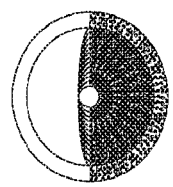
Figure 1:
Figure 1:
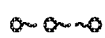
Figure 1:
Figure 1:

As a non-binding hypothesis to describe the effects of HMPGT materials to interact and solubilize poorly water-soluble (hydrophobic) or lipophilic APIs, the particulate structure of OHPP and its interactions with API molecules are shown in FIG. 1. The phytoglycogen forms a template (or a base) for grafting hydroxyalkyl (e.g., hydroxypropyl (HP)) chains, on which the hydrophobic or amphiphilic groups, such as octenyl succinate (OS), are further attached. In this invention, the hydroxyalkyl chains can also be polyalkylene glycol or polyalkylene oxide chains, such as polyethylene glycol (or polyethylene oxide) chains, or polypropylene glycol (or polypropylene oxide) chains.

In OHPP, both HP and OS groups are necessary for the performance of nanoparticles: (1) OS groups enhance the interactions between nanoparticles and hydrophobic API molecules, and (2) HP groups may offer OS groups the physical flexibility needed for effective interactions with API molecules. API molecules not only interact with OS groups at the surface of nanoparticles, but may also adsorb with the HP layer and possible PG (phytoglycogen) core.

Highly Branched Carbohydrate Polymers

In this invention, highly branched carbohydrate polymers can include highly branched alpha-D-glucans and other types of highly branched carbohydrate polymers.

The term "highly branched alpha-D-glucan" (highly branched α-D-glucan), as used herein, refers to a highly branched polysaccharide formed from alpha-D-glucose molecules, such as glycogen, phytoglycogen, amylopectin, or modified forms thereof. In some embodiments, the polysaccharides are linked by alpha-D-1,4 and alpha-D-1,6 glucosidic linkages. However, in other embodiments, chemical modification (e.g., pyrodextrinization) can be used to provide highly branched alpha-D-glucans including other types of linkages, such as alpha-D-1,2 and alpha-D-1,3 linkages. The highly branched alpha-D-glucan can be obtained, derived, or extracted from a plant material, a microbe (e.g., bacterium), or a human or non-human animal, or synthesized from glucose, glucans, or other materials. In one example, the highly branched alpha-D-glucan can be one from the group that comprises glycogen, phytoglycogen, amylopectin, and/or modified forms thereof, such as with modifications with octenyl succinate (OS) or polyethylene glycol (PEG).

In addition to alpha-D-glucans, other types of highly branched carbohydrate polymers can also be modified to provide capability to increase the solubility of poorly water-soluble compounds. The highly branched carbohydrate polymer can also be a non-glucan highly branched material, such as gum Arabic or its derivative, or arabinoxylan or its derivative. The carbohydrate polymer can also be a synthesized material such as polydextrose or its derivative. Furthermore, the carbohydrate polymer can be a material that is a "hybrid," for example, the material formed through covalent connections between two types of polysaccharide, between a polysaccharide and a protein (or a lipid), or between a polysaccharides and a monosaccharide (or a oligosaccharide).

As used herein, a highly branched carbohydrate polymer is a carbohydrate polymer having a branch density of at least about 4%. In some embodiments, the branch density of the highly branched carbohydrate polymer can range from about 5% to about 30%. In other embodiments, the branch density is at least 5%, at least 6%, at least 7%, or at least 8%. In other embodiments, the branch density can range for example, between about 7% to about 16%. For example, the branch density of amylopectin can be about 4%-6%, and the branch density of glycogen and phytoglycogen can be about 8%-11%. For example, for glucans that contain only alpha-D-1,4 and alpha-D-1,6 glucosidic linkages, branch density can be determined by comparing the number of alpha-D-1,4 and alpha-D-1,6 glucosidic linkages as follows: percentage branch density=the number of alpha-D-1,6 glucosidic linkages/(the number of alpha-D-1,4 glucosidic linkages+the number of alpha-D-1,6 glucosidic linkages)*100. In general, branch density is the percentage of the number of branching points based on all glycosidic linkages in the macromolecule.

For carbohydrate polymers or polysaccharides in general, branch density is the percentage of the number of branching points based on all glycosidic linkages in the macromolecule.

In some embodiments, the highly branched carbohydrate polymer (e.g., highly branched alpha-D-glucan) has a dendritic or dendrimer-like structure. In a dendritic or dendrimer-like structure, the polysaccharide chains are organized globularly like branches of a tree originating from a central location that acts as a primer at the core of the structure.

The branch density of a carbohydrate polymer can be determined by a number of methods, such as reducing end analysis, NMR, and chromatographic analysis. See Shin et al., Journal of Agricultural and Food Chemistry, 56: 10879-10886 (2008); Yao et al., Plant Physiology, 136: 3515-3523 (2004); and Yun and Matheson, Carbohydrate Research, 243: 307-321 (1993). Enzymatic treatment can affect the branch density of alpha-D-glucan by creating or cleaving alpha-D-1,4-glucosidic linkages and/or alpha-D-1,6-glucosidic linkages. These enzymes can be alpha-amylase, beta-amylase, debranching enzymes (e.g., pullulanase and isoamylase), transglucosidase, amyloglucosidase, and the like. Other approaches, such as acid or alkaline treatment, as well as oxidation can also affect the branch density of alpha-D-glucans. In one example, the highly branched alpha-D-glucan can be a single type of highly branched alpha-D-glucan. Alternately, the highly branched alpha-D-glucan can be a mixture that includes a plurality of different highly branched alpha-D-glucans.

In some embodiments, the highly branched carbohydrate polymer is a phytoglycogen. Phytoglycogen is a water-soluble, glycogen-like alpha-D-glucan generated by plants. One of the largest sources of phytoglycogen is the kernel of the maize mutant sugary-1 (su1), a major genotype of sweet corn. The su1 mutation leads to the deficiency of SU1, an isoamylase-type starch debranching enzyme (DBE) (James et al., Plant Cell, 7: 417-429 (1995)). In the biosynthesis of starch, starch synthase, starch branching enzyme and DBE work coordinately to produce starch granules (Yao, "Biosynthesis of starch," Comprehensive Glycoscience, edited by Hans Kamerling. Elsevier (2007)). It is considered that a role of DBE is to trim abnormal branches that inhibit the formation of starch crystals and granules. See Myers et al. Plant Physiology, 122: 989-997 (2000) and Nakamura, Plant and Cell Physiology, 43: 718-725 (2002). In the absence of DBE, the highly branched phytoglycogen is formed to replace starch granules.

Each phytoglycogen particle contains hundreds or thousands of glucan chains forming a highly packed structure. The highly branched structure of phytoglycogen results in its unusually high molecular density in dispersion. In rice, the dispersed molecular density of phytoglycogen is over 10 times that of starch (Wong et al., Journal of Cereal Science, 37: 139-149 (2003)). The molecular density of phytoglycogen from maize is around 1198 g/mol·nm$^3$ compared with about 62 g/mol·nm$^3$ for amylopectin of starch (Huang & Yao, Carbohydrate Polymers, 83, 1665-1671 (2011)). High density renders structural integrity of phytoglycogen and allows for dense grafting of functional groups. While not fully understood, it is likely that the phytoglycogen nanoparticles grow from the non-reducing ends of glucan chains at the surface by periodic branching and elongation of chains.

In some embodiments, the highly branched carbohydrate polymer is a modified highly branched alpha-D-glucan that has been subjected to the treatment of amyloglucosidase to reduce the particle size. One example is that phytoglycogen is subjected to amyloglucosidase to reduce its particle size from over 40 nm to below 30 nm.

Modified Highly Branched Carbohydrate Polymers

In some embodiments, the highly branched carbohydrate polymer is a modified highly branched carbohydrate polymer. A modified highly branched carbohydrate polymer is a highly branched carbohydrate polymer that has been modified by using chemical approaches, enzymatic approaches, physical approaches, biological approaches, or a combination of above. Through these modifications, the highly branched carbohydrate polymer (e.g., highly branched alpha-D-glucan) can have a different electrical charge, different hydrophobicity, an altered molecular weight, increased or decreased side chain length, a chemical or biochemical functional group, a reduced or increased branch density, altered particle size, or a combination thereof.

In some embodiments, the highly branched carbohydrate polymer has been modified to include functional groups selected from acetate, phosphate, octenyl succinate, succinate, hydroxypropyl, hydroxyethyl, cationic groups such as those containing quaternary ammonium cations (e.g. formed using 2,3-epoxypropyl trimethylammonium chloride, EPTAC, and (3-chloro-2-hydroxypropyl) trimethylammonium chloride, CHPTAC), carboxymethyl, polyethylene glycol (PEG, or polyethylene oxide), polypropylene glycol (or polypropylene oxide), or a combination of above.

In some embodiments, the highly branched carbohydrate polymer can also be modified using bleaching, acid hydrolysis, oxidation, pyrodextrinization, or a combination of above.

In some embodiments, the highly branched carbohydrate polymer can also be treated using shear force, high pressure processing, homogenization, hydrothermal processing, microwave, radiation, dry heating, or a combination of above.

In some embodiments, the highly branched carbohydrate polymer can be further treated by conjugating with bioactive or functional groups or ligands such as antibody, antigen, aptamer, protein, peptide, amino acid, cyclodextrin, saccharide, lipid, nucleic acid and nucleotide, folic acid (or folate), dendrimer, enzyme, fluorescent group or dye, magnetic group, metal ion, metal nanoparticle, quantum dot, polymer and block co-polymer, radioactive group, or a combination of above.

In some embodiments, highly branched carbohydrate polymers can be modified using enzymes such as alpha-amylase, beta-amylase, debranching enzymes (e.g., pullulanase and isoamylase), transglucosidase, amyloglucosidase, protease, and the like, or a combination of above.

In some embodiments, modification of highly branched carbohydrate polymers can be performed using a combination of enzymatic, physical, chemical, biological, or other methods mentioned above. Modified highly branched carbohydrate polymers can have different solubility characteristics, such as increased solubility in non-aqueous solvents such as ethanol, and can have solubility, the dissolution rate, and/or other properties associated with its environment, such as pH, ionic strength, temperature, biological environment, presence of magnetic field or various types of radiation, or a combination of above.

Hydrophobically modified phytoglycogen or glycogen-type (HMPGT) materials, hydrophobic highly branched alpha-D-glucans (HHBG), hydrophobic highly branched polysaccharides (HHBP), and hydrophobic highly branched carbohydrate polymers (HHBCP) are the solubilizing agents described by the current invention. These materials have potential to improve the water solubility of poorly water-soluble compounds. Phytoglycogen or glycogen-type materials are included within the scope of highly branched alpha-D-glucans. The treatment of other highly branched polysaccharides and/or highly branched carbohydrate polymers are largely the same as for highly branched alpha-D-glucans, except that specific enzymes need to be selected for achieving desirable enzymatic modifications of specific carbohydrate polymer or polysaccharide.

Solute Compounds

In one aspect, the invention described herein provides compositions for increasing the solubility of a hydrophobic solute compound (also referred as solute compound). It should be noted that the term "solute compound" is used herein as a convenient label, but that the modified highly branched carbohydrate polymers can be used for purposes other than increasing solubility, such as the physical, chemical, or physicochemical stability of the solute compound. Physical stability includes the stability of a solute compound in terms of its amorphous form, crystal size, crystalline structure or form (e.g. polymorphs), or a combination thereof. Chemical stability includes the stability of a solute compound in terms of its resistance to oxidation, reduction, chemical reaction, structure change or degradation, or a combination thereof. Physicochemical stability includes physical stability, chemical stability, or a combination thereof.

A wide variety of different hydrophobic solute compounds can be used. Many bioactive compounds are highly hydrophobic, meaning that they are likely to be soluble in lipids (oils) and/or some organic solvents, while being substantially insoluble in aqueous solution. The lack of solubility of bioactive compounds in aqueous solution is an important factor limiting their therapeutic applications. The present invention provides a solubilizing agent (modified highly branched carbohydrate polymers or polysaccharides) having sufficient affinity to associate with these hydrophobic solute compounds, while still remaining water soluble themselves. In addition, the solubilizing agent in present invention may increase the stability of the solute compound in the soluble composition, a composition that includes at least one modified highly branched carbohydrate polymer and at least one solute compound.

In another aspect, some hydrophobic solute compounds, such as griseofulvin, have strong crystalline structure. The thermodynamically stable crystalline structure drives quick transformation of amorphous form of compounds toward crystallization, leading to a low stability of amorphous form. When these compounds are associated with highly branched carbohydrate polymer or it derivatives, the rate of crystallization can be reduced. This will contribute to the increased stability and solubility of the solute compounds. In other cases, some solute compounds are easy to be oxidized or degraded, such as lemon oil and vitamin E. When these compounds are associated with highly branched carbohydrate polymer or its modified forms, the rate of oxidation can be reduced.

In general, the hydrophobic solute compound can include any one or combination of materials for which their improved solubility or the dissolution rate in an aqueous solution (e.g., water) is desirable. Due to their low solubility or low dissolution rate in water, these compounds have limited accessibility and bioavailability when used alone. The compositions of this invention can therefore include at least one hydrophobic solute compound having a water solubility and/or dissolution rate that is greater than the water solubility and/or dissolution rate of the solute compound in the absence of the highly branched carbohydrate polymer or the modified form thereof. In some instances, the hydrophobic solute compound can be a compound or a mixture of compounds selected from the group consisting of nutrients, vitamins, drugs, coloring agent, agrochemicals, pesticides, herbicides, anti-oxidants, coloring agents, hormones, essential oils, extracts from plants, Chinese medicine, animals or microbial organisms, and combinations thereof.

Hydrophobic solute compounds can be categorized in a variety of different manners. In some instances, the highly branched carbohydrate polymer or the modified forms thereof can be used together with relatively large solute compounds having a size from about 10,000 daltons to about 100,000 daltons. In other embodiments, the solute compound has a molecular weight or average molecular weight less than about 10,000 Daltons. In further embodiments, the solute compound has a molecular weight or average molecular weight of less than about 1,000 daltons. In other embodiments, the solute compound is a bioactive hydrophobic compound. Examples of hydrophobic compounds include phytochemicals, carotenoids, extracts from plants, animals, or microorganisms, and drugs.

Phytochemicals include phenolic compounds such as catechins, curcumin, quercetin, rutin, resveratrol, genistein, daidzein, and kaempferol; and carotenoids, e.g., lycopene, beta-carotene, and lutein.

Extracts from plant, animals, or microbial organisms (e.g., dietary supplements or medical extracts), include extracts from grape seeds, pomegranate, olive leaves, Turmeric, green tea, black tea, cocoa (cacao), insects, crustaceans, yeast, fungus, mushrooms, ginseng, cloves, Purslane, Acanthopanax, Rubescens, Pueraria, Ganoderma lucidum, Alisma, Medlar, Angelica, Gardenia, Honeysuckle, Sophora japonica, Flavescens, Schisandra, Cassia seed, Salvia, Radix, Epimedium, Licorice, Bupleurum, Pulsatilla, Houttuynia, Coptis, Artemisia annua, Scutellaria, Codonopsis, Forsythia, Camptotheca acuminate, and Andrographis paniculata.

The hydrophobic solute compounds of the invention can be an active pharmaceutical ingredient (API, e.g., a drug) such as a hydrophobic drug that is otherwise difficult to administer. Drugs include antineoplastic agents, such as paclitaxel, camptothecin, sagopilone, docetaxel, rapamycin, doxorubicin, daunorubicin, idarubicin, epirubicin, capecitabine, mitomycin c, amsacrine, busulfan, tretinoin, etoposide, chlorambucil, chlormethine, melphalan, and benzylphenylurea compounds; steroidal compounds, such as natural and synthetic steroids, and steroid derivatives, such as cyclopamine; antiviral agents, such as aciclovir, indinavir, lamivudine, stavudine, nevirapine, ritonavir, ganciclovir, saquinavir, lopinavir, and nelfinavir; antifungal agents, such as itraconazole, ketoconazole, miconazole, oxiconazole, sertaconazole, amphotericin b, and griseofulvin; antibacterial agents, such as quinolones, e.g., ciprofloxacin, ofloxacin, moxifloxacin, methoxyfloxacin, pefloxacin, norfloxacin, sparfloxacin, temafloxacin, levofloxacin, lomefloxacin, and cinoxacin; antibacterial agents, such as penicillins, e.g., cloxacillin, benzylpenicillin, and phenylmethoxypenicillin; antibacterial agents, such as aminoglycosides, e.g., erythromycin and other macrolides; antitubercular agents, such as rifampicin and rifapentine; and anti-inflammatory agents such as ibuprofen, indomethacin, ketoprofen, naproxen, oxaprozin, piroxicam, and sulindac.

In some embodiments, the hydrophobic solute compounds are active pharmaceutical ingredients with low or poor water solubility, such as acetaminophen, acetazolamide, albendazole, amiodarone, amphotericin, atorvastatin, azithromycin, azathioprine, bicalutamide, carbamazepine, carvedilol, cefdinir, cefprozil, celecoxib, chlorpromazine, chlorothiazide, cisapride, clarithromycin, clofazamine, clopidogrel, colistin, cyclosporine, cyproterone, danazol, dapsone, diclofenac, diflunisal, diloxanide, efavirenz, ezetimibe, fenofibrate, flurbiprofen, furosemide, glibenclamide, glimepiride, glipizide, glyburide, griseofulvin, haloperidol, hydrochlorothiazide, hydroxyzine pamoate, ibuprofen, imatinib mesylate, irbesartan, isotretinoin, indinavir, indomethacin, itraconazole, ivermectin, ketoconazole, ketoprofen, lansoprazole, lamotrigine, linezolid, lopinavir, lovastatin, loratadine, medroxyprogesterone acetate, meloxicam, metaxalone, methylphenidate hydrochloride, modafinil, moxifloxacin hydrochloride, mycophenolate mofetil, mebendazole, mefloquin, nalidixic acid, naproxen, neomycin, nevirapine, nelfinavir, nifedipine, niclosamide, nystatin, ofloxacin, olanzapine, oxcarbazepine, oxycodone hydrochloride, oxaprozin, orlistat, phenazopyridine, phenytoin, piroxicam, praziquantel, pioglitazone hydrochloride, pyrantel, quetiapine, raloxifene, retinol, rifampin, risperidone, ritonavir, rofecoxib, saquinavir, simvastatin, sirolimus, spironolactone, sulfamethoxazole, sulfasalazine, tacrolimus, tamoxifen, telmisartan, talinolol, terfenadine, trimethoprim, valdecoxib, valsartan, valproic acid, and warfarin.

In some embodiments, the hydrophobic solute compounds are cell culture components, including but not limited to one or more of following compounds: 6,7-ADTN HBr, R(−)-N-Allylnorapomorphine HBr, p-Aminoclonidine HCl, (±)-p-Aminoglutethimide, R(+)-Atenolol, S(−)-Atenolol, Butaclamol, Chloramphenicol, 4'-Chlordiazepam, Chlorthalidone, CNQX, Codeine sulfate, CV-1808, 8-Cyclopentyl-1,3-p-sulfophenylxanthine, Dexamethasone, Diazepam, Digoxin, 7,9-Dimethyluric acid, 7,9-Dimethylxanthine, 3,5-Dinitrocatechol, 1,3-Dipropyl-8-p-sulfophenylxanthine, DNQX, (S)-ENBA, Estradiol, FG-7142, Furosemide, L-Glutamic acid HCl, L-Glutamic acid diethyl ester HCl, Glutethimide, Haloperidol, Hexahydro-sila-difenidol HCl, Hexahydro-sila-difenidol HCl, p-fluoro analog, Hydrocortisone, 6-Hydroxydopamine HBr, 3-Hydroxymethyl-ß-carboline, Indomethacin, Iodotubercidin, Isobutylmethylxanthine, (−)-MDO-NPA HCl, Methotrexate, 2-Methylthio ATP, Naltrindole HCl, Quabain, Papaverine HCl, 2-Phenylaminoadenosine, R(−)-PIA, S(+)-PIA, Pirenperone, Prochlorperazine, Progesterone, DL(±)-Propranolol, (−)-Quisqualic acid, Ranitidine HCl, Ro 15-4513, Ro 20-1724, PDE inhibitor, Ro 41-0960, COMT inhibitor, Ryanodine, SKF-83566 HCl, Spiperone HCl, Sulpride, Testosterone, Tetrahydrocannabinol, Veratridine, Vitamin A, Vitamin D.

In some embodiments, the hydrophobic solute compound is a phenolic compound. Phenolic compound are substances that have one or more aromatic rings and bear one or more hydroxyl substituents on the ring, including functional derivatives such as esters, methyl ethers, glycosides and other derivatives that are apparent to those skilled in the art. Included in the definition of phenolics are polyphenols having complex substitution patterns, compounds having condensed rings, and phenolics containing one or more amine moieties and/or carboxylic acid moieties. Examples of naturally occurring phenolic compounds include, but are not limited to: bergaptol, caffeic acid, capsaicin, coumarin, daidzein, 2,5-dihydroxybenzoic acid, ferulic acid, flavonoids, glycitein (isoflavone), 4-hydroxycinnamic acid, 4-hydroxycoumarin, isopimpinellin, resveratrol, synapic acid, vanillic acid, and vanillin.

Synthetic and naturally-occurring phenolic moieties, some of which may contain amine groups, carboxylic acid groups, or aminoacids, are part of many drugs. Examples of these medicinal phenolic compounds include acenocoumarol, acetarsol, actinoquinol, adrenalone, alibendol, aminosalicylic acids, amodiaquine, anethole, balsalazide, bamethan, benserazide, bentiromide, benzarone, benzquinamide, bevantolol, bifluranol, buclosamide, bupheniode, chlorobiocin, chlorotrianisene, chloroxylenol, cianidanol, cinepazide, cinitapride, cinepazide, cinmetacin, clebopride, clemastine, clioquinol, coumermycin A1, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indometacin, ipriflavone, isoetarine, isoprenaline, isoxsuprine, itopride hydrochloride, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, novobiocin, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

In other embodiments, the hydrophobic solute compounds can be essential oils as crude or purified extracts of plants, individual compounds or their mixtures, and/or their corresponding synthetic substances. For example, thymol is a component of thyme oil. The essential oils can be agar oil, ajwain oil, angelica root oil, anise oil, asafoetida, balsam oil, basil oil, bay oil, bergamot oil, black pepper essential oil, birch, camphor, cannabis flower essential oil, caraway oil, cardamom seed oil, carrot seed oil, cedarwood oil, chamomile oil, calamus root oil, cinnamon oil, cistus species, citronella oil, clary sage, clove leaf oil, coffee, coriander, costmary oil, costus root, cranberry seed oil, cubeb, cumin oil/black seed oil, cypress, cypriol, curry leaf, davana oil, dill oil, elecampane, eucalyptus oil, fennel seed oil, fenugreek oil, fir, frankincense oil, galangal, galbanum, geranium oil, ginger oil, goldenrod, grapefruit oil, henna oil, helichrysum, hickory nut oil, horseradish oil, hyssop, idaho tansy, jasmine oil, juniper berry oil, *Laurus nobilis*, lavender oil, ledum, lemon oil, lemongrass, lime, litsea cubeba oil, mandarin, marjoram, melaleuca see tea tree oil, melissa oil (lemon balm), mentha arvensis oil/mint oil, mountain savory, mugwort oil, mustard oil, myrrh oil, myrtle, neem oil, neroli, nutmeg, orange oil, oregano oil, orris oil, palo santo, parsley oil, patchouli oil, perilla essential oil, peppermint oil, petitgrain, pine oil, ravensara, red cedar, roman chamomile, rose oil, rosehip oil, rosemary oil, rosewood oil, sage oil, sandalwood oil, sassafras oil, savory oil, schisandra oil, spearmint oil, spikenard, spruce oil, star anise oil, tangerine, tarragon oil, tea tree oil, thyme oil, tsuga, turmeric, valerian, vetiver oil, western red cedar, wintergreen, yarrow oil, ylang-ylang, zedoary.

In a preferred embodiment, the hydrophobic solute compound is a bioactive hydrophobic compound selected from one or more of a carotenoid, a curcuminoid, a flavonoid, a sterol, a phytosterol, a saponin, an aglycone, or an algycone of a saponin (i.e., a sapogenin). In a further embodiment, the solute compound can be selected from the group consisting of curcumin, quercetin, resveratrol, thymol, paclitaxel, ibuprophen, and griseofulvin.

In some embodiments, the solute compounds are hydrophobic vitamins, such as Vitamin A, Vitamin E, Vitamin D, and Vitamin K.

In some embodiments, the solute compounds are hydrophobic colorants, such as carotenoids, lutein, carmine, turmeric, cacao, annatto (bixin), paprika, hematoxylin, anthocyanins, lac dye, chlorophyllin, cochineal, lycopene.

Soluble Composition

In the present invention, a soluble composition is a combination of at least one solubilizing agent with at least one solute compound. A soluble composition realizes increased solubility of the soluble compound(s) in water-containing solvent and allows the preparation of aqueous solutions of a wide variety of concentrations. As the concentrated solutions can be diluted with an aqueous medium in any proportion and over a wide range of pH conditions without separation or precipitation of the hydrophobic compound, the solubility of the compound is maintained under physiological conditions, for example after an oral or parenteral administration of the composition. This normally results in an improved bioavailability of the solute compound.

The soluble compositions of the present invention can be easily incorporated into pharmaceutical, nutraceutical, medical, or cosmetic formulations in which the solute compound shows improved bioavailability. Such formulations may further contain additional active ingredients and/or a pharmaceutically or cosmetically acceptable additives or vehicles, including solvents, surfactants, adjuvants, texture agents, bulking agents, excipients, sweeteners, fillers, colorants, flavoring agents, lubricants, binders, moisturizing agents, preservatives and mixtures thereof. Collectively, these additional formulation materials can be referred to as the pharmaceutically acceptable carrier. "Pharmaceutically acceptable" as used herein means that the carrier is suitable for administration to a subject for the methods described herein, without unduly deleterious side effects. The formulations may have a form suitable for a topical (e.g., a cream, lotion, gel, ointment, dermal adhesive patch), oral (e.g., a capsule, tablet, caplet, granulate, powder, liquid), or parenteral (e.g., suppository, sterile solution) administration. Among the acceptable vehicles and solvents that may be employed for administration by injection are water, mildly acidified water, Ringer's solution and isotonic sodium chloride solution.

In other embodiments, the soluble compositions including a solute compound and a modified highly branched carbohydrate polymer can be incorporated into other types of formulations. Examples of these additional formulations include foods and beverages, food supplements, cell culture, agrochemicals such as fertilizers and pesticides, paint and coating, and the like. The formulation of such nutritional, agricultural, or chemical formulations is known to those skilled in the art.

According to the present invention, soluble compositions that contain bioactive hydrophobic compounds may be administered to a warm-blooded animal, particularly a human, in need of the prophylaxis or therapy. The dose of a bioactive hydrophobic compound and the corresponding dose of its soluble composition together with modified highly branched carbohydrate polymer for treating diseases or disorders will vary upon the manner of administration, the age, sex, the body weight of the subject, and the condition being treated, and will be ultimately decided by the attending physician or veterinarian. Such an amount of the bioactive compound in the form of its water-soluble composition as determined by the attending physician or veterinarian is referred to herein as a "therapeutically effective amount".

The mass ratio of solute compound to modified highly branched carbohydrate polymer can vary from about 100:1 to about 1:1000. The ratio of solute compound to modified highly branched carbohydrate polymer can vary depending on the type of composition being provided. For example, in compositions intended to stabilize a solute compound in dry form, a mass ratio ranging from about 100:1 to about 1:50 of solute compound to modified highly branched carbohydrate polymer can be used, with a mass ratio ranging from about 2:1 to about 1:20 being preferred. Alternately, in compositions for increasing the solubility of solute compound, a lower ratio of solute compound to modified highly branched carbohydrate polymer can be used. For example, for a soluble composition, a mass ratio ranging from about 10:1 to about 1:1000 of solute compound to carbohydrate polymer can be used, with a mass ratio ranging from about 1:1 to about 1:50 being preferred. The lower limit of the mass ratio is not critical, and the modified highly branched carbohydrate polymer can be used in any excess. However, this is not desirable in some applications, since increasing the amount of the modified highly branched carbohydrate polymer decreases the concentration of the active ingredient in the composition and in its aqueous solutions.

Use of Modified Highly Branched Carbohydrate Polymers to Increase Solubility, Dissolution Rate, and/or Stability Combination of the solubilizing agent, that is, highly branched carbohydrate polymers or modified forms thereof with the solute compound provides a variety of benefits. In some embodiments, the invention provides a method of increasing the solubility, the dissolution rate, and/or stability of a solute compound by combining the solute compound with an effective amount of the highly branched carbohydrate polymer.

The present disclosure provides a method of increasing the solubility and/or the dissolution rate of a solute compound. The method includes the steps of combining an effective amount of at least one highly branched carbohydrate polymer, or a modified form thereof, with a solvent, combining the solute compound with a second solvent, and adding the two together. In some embodiments, the solute compound and the highly branched carbohydrate polymer are first combined, and are then added to the solvent. However, the method need not follow the order in which these steps are described. In other words, in some embodiments, it may be preferable to add the solute compound to a solvent, and then add the highly branched carbohydrate polymer. The increased solubility is exhibited once the solute compound has been placed together with the highly branched carbohydrate polymer, in a process that involves the use of a solvent or no solvent. The solvent can be a relatively polar solvent, and in some embodiments is an aqueous solvent (e.g., water), and in some embodiments is a mixture of aqueous and non-aqueous solvent. As described herein, addition of the highly branched carbohydrate polymer to the solute compound results in the solute compound becoming associated or enmeshed in the branches of the carbohydrate polymer so that the solute compound is solubilized along with the highly branched carbohydrate polymer.

In some embodiments, to achieve enhanced solubility and/or dissolution rate of solute compounds, a solvent is not necessary for combining a solute compound with a highly branched carbohydrate polymer or its modified form, since this highly branched carbohydrate polymer or its modified form can interact, dissolve, or adsorb solute compounds without the use of a solvent. The processing for such a non-solvent combination can be assisted with extrusion, pressing, homogenization, grinding, rolling, kneading, ultrasonication, or a combination of above.

Use of the highly branched carbohydrate polymer (e.g., phytoglycogen) or its modified forms can increase the solubility of the solute compounds to a varying degree, depending on the particulars of the solute compound, the highly branched carbohydrate polymer or its modified forms, and the solution in which the solute compound is placed. For example, in some embodiments the method increases the solubility of the solute compound by at least about a factor of two relative to the solubility of the solute compound in the absence of the highly branched carbohydrate polymer. In other words, in some instances, the solute compound can have a solubility that is at least two times greater than the solubility of the solute compound in the absence of a highly branched carbohydrate polymer. In other instances, the solute compound can have a solubility that is at least five times greater than the solubility of the solute compound in the absence of a highly branched carbohydrate polymer. In further instances, the solute compound can have a water solubility that is at least ten times greater than the solubility of the solute compound in the absence of the highly branched carbohydrate polymer, and in yet further embodiments, the solubility of the solute compound is at least one hundred times greater when combined with the highly branched carbohydrate polymer.

Phenolic compounds are one type of solute compound whose solubility is significantly enhanced by highly branched carbohydrate polymers or their modified forms. The present invention is capable of increasing the solubility of some phenolic compounds by at least ten times compared with their solubility in the absence of the highly branched carbohydrate polymers. For example, use of OHPP can increase the solubility of curcumin in aqueous solution by at least 100 times, and can increase the solubility of resveratrol in aqueous solution by at least 10 times.

In other embodiments, a method of increasing the stability of a solute compound is provided. The method includes the steps of adding an effective amount of at least one highly branched carbohydrate polymer, or a modified form thereof, to the solute compound and combining the solute compound with a solvent. As with the methods for increasing solubility, the steps of this method can be carried out in any order. The solute compound complexed with the highly branched carbohydrate polymer or its modified forms thereof is more resistant to crystallization, oxidation, reduction, structure change, deterioration and degradation, enzyme reaction, chemical reaction, or a combination thereof, than the solute compound in the absence of a highly branched carbohydrate polymer. In addition, because crystallization lowers the solubility and/or dissolution rate of solute compounds, stabilization of the solute compounds in a non-crystallized form improves solubility and/or dissolution rate. Compositions including a solute compound and the highly branched carbohydrate polymer show an excellent stability over long periods of time, in one embodiment, for over a month in room temperature, in another embodiment, for over one year.

In some embodiments, for enhanced stability of solute compounds, a solvent may not be necessary for combining a solute compound with an HMPGT material that can interact, dissolve, or adsorb solute compounds. The processing for such a non-solvent combination can be extrusion, pressing, homogenization, grinding, rolling, kneading, ultrasonication, or a combination of above.

Preparation of Soluble Compositions that Contain Solute Compounds and HMPGT Materials Another aspect of the invention involves methods for preparing a soluble composition. In one embodiment, the method includes dissolving the hydrophobic solute compound in a solvent to form a solution; mixing the solution with the HMPGT material, or a modified form thereof; and removing the solvent to obtain the soluble composition. In some embodiments, the solvent is a mixture of non-aqueous solvent and aqueous solvent.

In another embodiment, the method for preparing a soluble composition includes the steps of dissolving or dispersing at least one hydrophobic solute compound in a first solvent to form a first solution or dispersion; dissolving or dispersing at least one HMPGT material or a modified form thereof in a second solvent to form a second solution or dispersion; mixing the first and second solutions or dispersions together to form a mixture; and removing the solvent from the mixture to obtain a composition; wherein the water solubility of the solute compound in the composition is greater than the water solubility of the hydrophobic solute compound in the absence of the at least one HMPGT material or a modified form thereof. In some embodiments, the first solvent can be an aqueous solvent; in some embodiments, the first solvent can be a non-aqueous solvent; in some embodiments, the first solvent can include a mixture of non-aqueous solvent and an aqueous solvent. In further embodiments, the second solvent can be an aqueous solvent; in some embodiments, the second solvent can be a non-aqueous solvent; in some embodiments, the second solvent can include a mixture of a non-aqueous solvent and an aqueous solvent.

In other embodiment, the method for preparing a soluble composition includes the steps of combining at least one hydrophobic solute compound with at least one HMPGT material or a modified form thereof. The combination can be in a solvent, or without any solvent.

In some embodiments, the solvent is a non-aqueous solvent. Examples of non-aqueous solvents can be selected from the group consisting of pentane, cyclopentane, hexane, cyclohexane; benzene; toluene; 1,4-dioxane, chloroform, diethyl ether, dichloromethane, tetrahydrofuran, ethyl acetate, acetone, dimethylformamide, acetonitrile, dimethyl sulfoxide, formic acid, n-butanol, isopropanol, n-propanol, ethanol, methanol, acetic acid, and combinations thereof. In some embodiments, the solvent can be a non-aqueous solvent. In some embodiments, the solvent can include a mixture of non-aqueous solvent and an aqueous solvent.

In some embodiments, the soluble composition including the hydrophobic solute compound and the HMPGT material or a modified form thereof can be prepared with additional processing steps. For example, in some embodiments, the HMPGT material is derived or extracted from a plant source, an animal source, or a microbial source, or synthesized, or a combination thereof. In additional embodiments, preparation of the soluble composition further includes the step of processing the mixture by kneading, extrusion, homogenization, ultrasonic, high-pressure treatment, high-speed treatment, microwave treatment, radiation treatment, heat treatment, or a combination thereof. In yet further embodiments, the method includes removing the solvent from the mixture by spray drying, vacuum drying, freeze drying, drum drying, heat drying, extrusion, supercritical extraction, or a combination thereof.

When combining hydrophobic solute compounds with HMPGT materials, it can sometimes be challenging to find a single solvent in which both carrier and solute compound are soluble. DMSO is a particularly effective solvent in this regard, but it can be difficult to remove DMSO after complexation. In these situations, it may be preferable to prepare a form of HMPGT material that is soluble in ethanol, acetone, or this type of low polar or non-polar solvent. For example, phytoglycogen has been modified into phytoglycogen octenyl succinate (PG-OS), which can be dissolved in non- or low-polarity solvents. To further improve the solubility of carbohydrate polymer, polyethylene glycol (PEG) chains can be added on PG-OS, thus generating PG-OS-PEG. This new material has much enhanced solubility than PG-OS. In another example, phytoglycogen can be modified to generate OHPP which is soluble in both water and ethanol.

In some embodiments, a solvent is not necessary for combining a solute compound with a HMPGT material or its modified form, since this HMPGT material or its modified form can interact, dissolve, or adsorb solute compounds without the use of a solvent. The processing for such a non-solvent combination can be assisted with blending, extrusion, pressing, tableting, homogenization, grinding, rolling, kneading, ultra-sonication, or a combination of above.

The present invention is illustrated by the following examples. It is to be understood that the particular examples, materials, amounts, and procedures are to be interpreted broadly in accordance with the scope and spirit of the invention as set forth herein.

EXAMPLES

Example 1: Preparation of Octenylsuccinate Hydroxyethyl Phytoglycogen (OHEP)

Ten grams of phytoglycogen (PG) was dispersed in 60 g deionized water. Forty grams sodium hydroxide (NaOH) was dissolved in 100 g deionized water. The PG dispersion and NaOH solutions were mixed and added in a 2-liter glass reactor. The temperature was adjusted to 4° C. and $N_2$ gas was bubbled into the solution (till the end of reaction). Cold (ice-water preserved) ethylene oxide (ETO) 270 ml was added in the dispersion over the 72 h reaction, with 90 mL added within each 24 h. After each addition of ETO, the system was allowed to stay at 4° C. for 15 min, 10° C. for 20 min, and the temperature was increased to 30° C. before next addition of ETO.

After 72 h reaction, the reactant was neutralized with acetic acid (HAc) and then subjected to ultrafiltration (MWCO 300 kD, Centramate, Pall Life Science) to remove small molecules. For each of 10 cycles of ultrafiltration, the volume of product was reduced to ½ and then added with deionized water to reach its original volume. The permeated liquid was discarded. The final product of ultrafiltration (as retentate) was considered as the dispersion of purified hydroxyethyl phytoglycogen (HEP).

Half of the purified HEP dispersion was used for the grafting of octenyl succinate group. To carry out the reaction, the HEP dispersion was adjusted to pH 8.5-9.0 using NaOH. To the dispersion, 6 g octenyl succinic anhydride (OSA) was added in 4 h. After 15 h from the OSA addition, the reaction was terminated through adjusting to pH6.0. The reactant was purified using ultrafiltration to collect the dispersion of octenylsuccinate hydroxyethyl phytoglycogen (OHEP). The OHEP dispersion was lyophilized (freeze-dried) to collect OHEP solid.

Example 2: Preparation of Octenylsuccinate Hydroxyethyl Phytoglycogen (OHEP)

Fifty grams of phytoglycogen (PG) was dispersed in 300 g deionized water. One hundred and fifty grams sodium hydroxide (NaOH) was dissolved in 300 g deionized water. The PG dispersion and NaOH solutions were mixed and added in a 2-liter glass reactor. The temperature was adjusted to 4° C. and $N_2$ gas was bubbled into the solution (till the end of reaction). Cold (ice-water preserved) ethylene oxide (ETO) 1,200 mL was added in the dispersion over the 72 h reaction, with 400 mL added within each 24 h. After each addition of ETO, the system was allowed to stay at 4° C. for 15 min, 10° C. for 20 min, and the temperature was increased to 30° C. before next addition of ETO.

At the point of 72 h, reactant was collected and neutralized with acetic acid, and then subjected to ultrafiltration (MWCO 300 kD) to obtain the dispersion of purified HEP.

Four fifth of the purified HEP dispersion was adjusted to pH 8.5-9.0 using NaOH. To the dispersion, 60 g octenyl succinic anhydride (OSA) was added in 4 h. After 15 h from the last OSA addition, the reaction was terminated through adjusting to pH 6.0. The reactant was purified using ultrafiltration to collect the dispersion of octenylsuccinate hydroxyethyl phytoglycogen (OHEP). The OHEP dispersion was lyophilized to collect OHEP solid.

Example 3: Preparation of Octenylsuccinate Hydroxypropyl Phytoglycogen (OHPP)

Fifty grams of phytoglycogen (PG) was dispersed in 300 g deionized water. One hundred and fifty grams sodium hydroxide (NaOH) was dispersed in 300 g deionized water. The PG dispersion and NaOH solutions were mixed, heated in boiling water bath for 1 h, and then added in a 2-liter glass reactor. The temperature was adjusted to 10° C. and $N_2$ gas was bubbled into the solution for 30 min. To the PG dispersion, propylene oxide 250 mL was added and the temperature was increased to 20° C. for the reaction to proceed for 15 h. The reactant was then collected and neutralized with acetic acid, and then subjected to ultrafiltration (MWCO 300 kD) to obtain the dispersion of purified hydroxypropyl phytoglycogen (HPP).

Half of the purified HPP dispersion was used for grafting octenyl succinate group. Another half of purified HPP dispersion was subjected to a second round of reaction with 125 mL propylene oxide. After reaction, the product was purified using ultrafiltration.

Each of the purified HPP dispersions collected from the first and second batches was adjusted to pH 8.5-9.0. To each dispersion, 30 g octenyl succinic anhydride (OSA) was added to prepare octenylsuccinate hydroxypropyl phytoglycogen. The reactants generated were subjected to ultrafiltration and lyophilization to collect the solid product of octenylsuccinate hydroxypropyl phytoglycogen (OHPP).

Example 4: Preparation of Phytoglycogen β-Dextrin (PBD) and OHPPBD (Octenylsuccinate Hydroxypropyl Phytoglycogen Beta-Dextrin)

One hundred grams of PG was dispersed in 500 mL sodium acetate (NaAc) buffer (pH 6.0, 50 mM). To this dispersion, 1 mL barley β-amylase (28,400 U/mL, Megazyme) was added. The reaction was carried out 50° C. for 24 h in a shaking water bath. Thereafter, the reactant was added into 2 L ethanol to terminate the reaction and precipitate hydrolyzed PG (PG beta-dextrin). The precipitated solid was repetitively washed using 80% ethanol, dehydrated using pure ethanol, filtered, and hood-dried to collect solid of PG beta-dextrin (PBD).

The procedure to prepare OHPPBD using PBD was the same as that for preparing OHPP using PG. Briefly, PBD dispersed in NaOH solution was added with propylene oxide, and the reaction was allowed to proceed for 24 h. Thereafter, the reactant was neutralized and subjected to ultrafiltration to purify hydroxypropyl phytoglycogen beta-dextrin (HPPBD). The purified HPPBD dispersion was added with propylene oxide for additional substitution for 24 h, which was followed by neutralization and ultrafiltration to purify HPPBD generated. Thereafter, the purified HPPBD dispersion was added with octenyl succinic anhydride, and the product generated was subjected to ultrafiltration and lyophilization to obtain the solid of octenylsuccinate hydroxypropyl phytoglycogen beta-dextrin (OHPPBD).

Example 5: Preparation of Propionate Hydroxypropyl Phytoglycogen (PHPP), Acetate Hydroxypropyl Phytoglycogen (AHPP), and Propionate Octenylsuccinate Hydroxypropyl Phytoglycogen (POHPP)

The procedure of preparing hydroxypropyl phytoglycogen (HPP) was the same as described in earlier examples. Ultrafiltration was used to obtain purified HPP dispersion.

To prepare PHPP, propionic anhydride was added to the HPP dispersion (pH 8.5-9.0, 40° C.), and the substitution reaction was allowed to proceed for 24 h. The product generated was subjected to neutralization, ultrafiltration, and lyophilization to collect the PHPP solid.

To prepare AHPP, acetic anhydride was added to the HPP dispersion (pH 8.5-9.0, 40° C.), and the substitution reaction was allowed to proceed for 24 h. The product generated was subjected to neutralization, ultrafiltration, and lyophilization to collect the AHPP solid.

To prepare POHPP, both propionic anhydride and octenyl succinic anhydride were added to the HPP dispersion (pH 8.5-9.0, 40° C.), and the substitution reaction was allowed to proceed for 24 h. The product generated was subjected to neutralization, ultrafiltration, and lyophilization to collect the POHPP solid.

Example 6: Increase of API Solubility Through their Complexation with OHPP

The performances of HMPGT, such as OHPP to improve the solubility of a number of APIs were highly effective. Below are examples with a number of APIs: niclosamide, paclitaxel, docetaxel, celecoxib, itraconazole, griseofulvin, and curcumin.

Example 6-1: Preparation of OHPP

Fifty grams of phytoglycogen (PG) was dispersed in 300 g deionized water. One hundred and fifty grams sodium hydroxide (NaOH) was dispersed in 300 g deionized water. The PG dispersion and NaOH solutions were mixed, heated in boiling water bath for 1 h, and then added in a 2-liter glass reactor. The temperature was adjusted to 10° C. and $N_2$ gas was bubbled into the solution for 30 min. To the PG dispersion, propylene oxide 250 mL was added and the temperature was increased to 20° C. for the reaction to proceed for 15 h. The reactant was then collected and neutralized with acetic acid, and then subjected to ultrafiltration (MWCO 300 kD) to obtain the dispersion of purified hydroxypropyl phytoglycogen (HPP). The purified HPP dispersion was then subjected to a second round of reaction with 250 mL propylene oxide. After reaction, the product was purified using ultrafiltration.

The purified HPP dispersion was adjusted to pH 8.5-9.0 using NaOH, and 65 g octenyl succinic anhydride (OSA) was added to prepare octenylsuccinate hydroxypropyl phytoglycogen. The reactant generated was subjected to ultrafiltration and lyophilization to collect the solid product of octenylsuccinate hydroxypropyl phytoglycogen (OHPP).

The OHPP materials generated using this procedure were used in a number of experiments, including DS determination using NMR, API incorporations, solubility evaluations, caco-2 monolayer permeation, and anti-cancer efficacy evaluations.

Example 6-2: Solubility of Niclosamide, with API/Excipient Ratio of 1/3

One part of niclosamide was physically incorporated with 3 parts of OHPP, and the final product was in solid form. The combined material between niclosamide and OHPP is termed as "niclosamide-OHPP complex", "Nic-OHPP complex", or "Nic-OHPP" in the present invention. Similarly the physically combined material between niclosamide and HPMCAS is termed as "niclosamide-HPMCAS complex", "Nic-HPMCAS complex", or "Nic-HPMCAS"; the physically combined material between niclosamide and Soluplus (BASF) is termed as "niclosamide-Soluplus complex", "Nic-Soluplus complex", or "Nic-Soluplus".

Hydroxypropyl methylcellulose acetate succinate (HPMCAS) was developed earlier as an enteric film coating because it is insoluble in acidic gastric fluid, but may swell and dissolve in the small intestine. Recently, it has been used to improve the solubility of poorly water-soluble APIs.

Soluplus (Soluplus®, BASF) was developed to form solid dispersions with poorly soluble drug substances to improve their solubility and bioavailability. Soluplus is a synthetic polymer with an amphiphilic chemical structure, allowing it to act as a matrix polymer in solid dispersion of drugs and also solubilize drugs in aqueous media. Soluplus is a polyvinyl caprolactam-polyvinyl acetate-polyethylene glycol copolymer (MW around 118,000 g/mol), having a PEG backbone with one or two sides chains consisting of vinyl acetate copolymerized with vinyl caprolactam.

In this document, both HPMCAS and Soluplus were used as references to evaluate the performance of OHPP in solubilizing poorly water-soluble APIs in aqueous systems.

To evaluate the solubility of niclosamide in aqueous system, 10 mg of each complex or 2.5 mg niclosamide alone was mixed with 1.0 mL Hank's Balanced Salt Solution (HBSS) under constant agitation for 2 h in a shaking water bath (37° C., 100 rpm). Thereafter, the dispersions were centrifuged at 16,000 g for 10 min, and the supernatants were collected for niclosamide quantification using HPLC. The concentration of niclosamide in the supernatant was considered as its water solubility.

Figure 2:
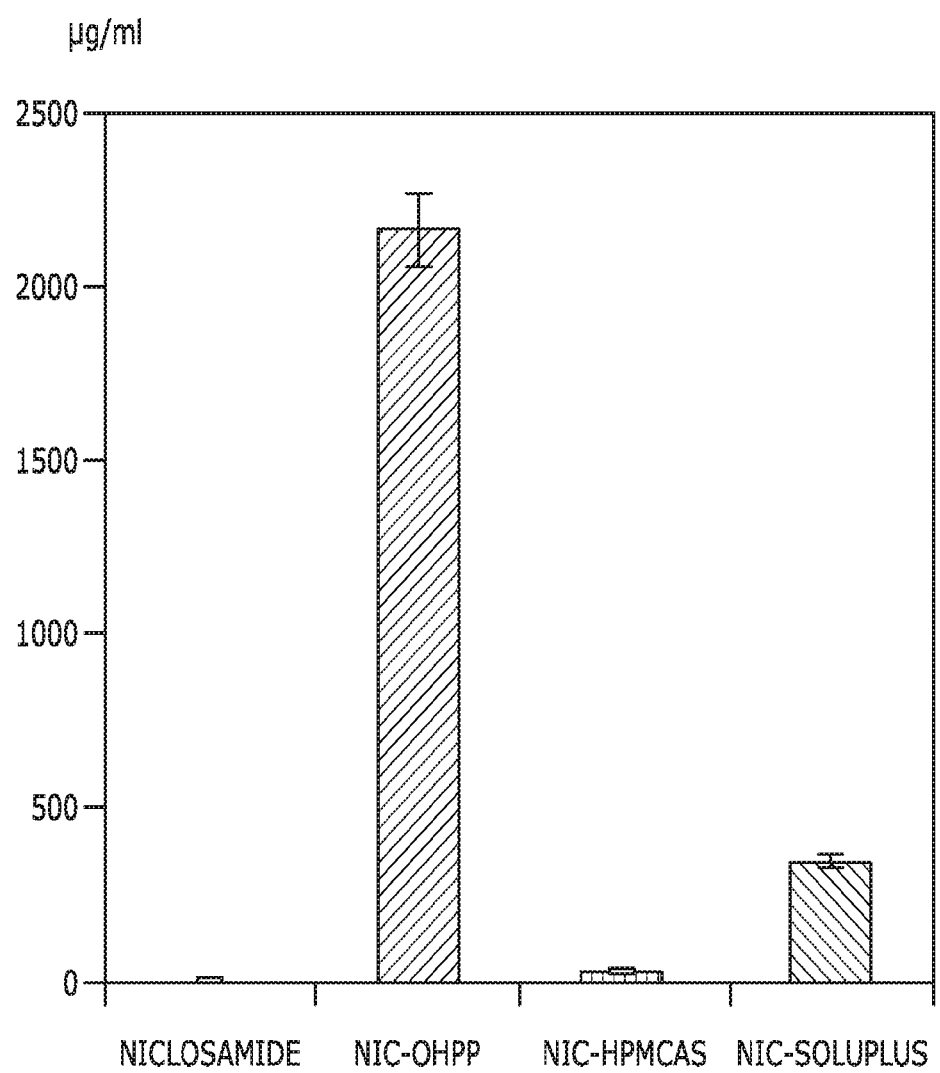
FIG. 2 provides a graph showing the solubility of niclosamide when incorporated with OHPP, HPMCAS, and Soluplus (Soluplus®, BASF), as compared with that of niclosamide alone. The ratio between niclosamide and excipient was 1/3, with total dispersed API of 2,500 µg/mL in HBSS buffer (37° C.). The mixing time was 2 h before subjecting the dispersion to centrifugation to collect supernatant for API quantification.

The water solubility of niclosamide for niclosamide alone, Nic-OHPP, Nic-HPMCAS, and Nic-Soluplus are compared in FIG. 2. The solubility of niclosamide was around 2,178 µL/mL with Nic-OHPP, much greater than that of niclosamide alone (around 13.2 µL/mL), Nic-HPMCAS (around 35.4 µL/mL), and Nic-Soluplus (around 353.8 µL/mL).

Example 6-3: Solubility of Paclitaxel, with API/Excipient Ratio of 1/3

One part of paclitaxel was physically incorporated with 3 parts of OHPP, and the final product was in solid form. The combined material between paclitaxel and OHPP is termed as "paclitaxel-OHPP complex", "Pac-OHPP complex", or "Pac-OHPP" in this document. Similarly the physically combined material between paclitaxel and HPMCAS is termed as "paclitaxel-HPMCAS complex", "Pac-HPMCAS complex", or "Pac-HPMCAS"; the physically combined material between paclitaxel and Soluplus is termed as "paclitaxel-Soluplus complex", "Pac-Soluplus complex", or "Pac-Soluplus".

To evaluate the solubility of paclitaxel in aqueous system, 10 mg of each complex or 2.5 mg paclitaxel alone was mixed with 1.0 mL Hank's Balanced Salt Solution (HBSS) under constant agitation for 2 h in a shaking water bath (37° C., 100 rpm). Thereafter, the dispersions were centrifuged at 16,000 g for 10 min, and the supernatants were collected for paclitaxel quantification using HPLC. The concentration of paclitaxel in the supernatant was considered as its water solubility.

Figure 3:
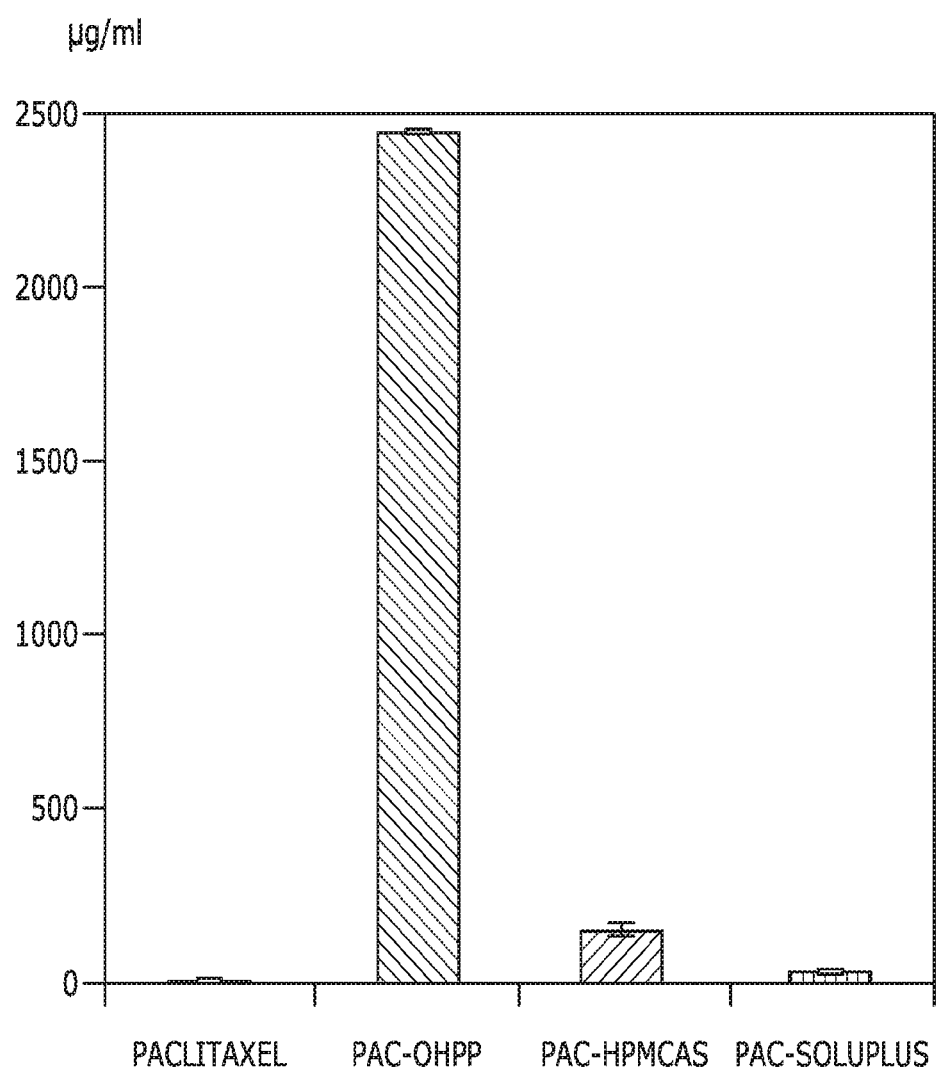
FIG. 3 provides a graph showing the solubility of paclitaxel when incorporated with OHPP, HPMCAS, and Soluplus, as compared with that of paclitaxel alone. The ratio between paclitaxel and excipient was 1/3, with total dispersed paclitaxel of 2,500 µg/mL in HBSS buffer (37° C.). The mixing time was 2 h before subjecting the dispersion to centrifugation to collect supernatant for paclitaxel quantification.

The water solubility of paclitaxel for paclitaxel alone, Pac-OHPP, Pac-HPMCAS, and Pac-Soluplus are compared in FIG. 3. The solubility of paclitaxel was around 2,469 µL/mL with Pac-OHPP, much greater than that of paclitaxel alone (around 6.2 µL/mL), Pac-HPMCAS (around 135.6 µL/mL), and Pac-Soluplus (around 20.8 µL/mL).

Example 6-4: Solubility of Griseofulvin, with API/Excipient Ratio of 1/3

One part of griseofulvin was physically incorporated with 3 parts of OHPP, and the final product was in solid form. The combined material between griseofulvin and OHPP is termed as "griseofulvin-OHPP complex", "Gri-OHPP complex", or "Gri-OHPP" in this document. Similarly the physically combined material between griseofulvin and HPMCAS is termed as "griseofulvin-HPMCAS complex", "Gri-HPMCAS complex", or "Gri-HPMCAS"; the physically combined material between griseofulvin and Soluplus is termed as "griseofulvin-Soluplus complex", "Gri-Soluplus complex", or "Gri-Soluplus".

To evaluate the solubility of griseofulvin in aqueous system, 10 mg of each complex or 2.5 mg griseofulvin alone was mixed with 1.0 mL Hank's Balanced Salt Solution (HBSS) under constant agitation for 2 h in a shaking water bath (37° C., 100 rpm). Thereafter, the dispersions were centrifuged at 16,000 g for 10 min, and the supernatants were collected for griseofulvin quantification using HPLC. The concentration of griseofulvin in the supernatant was considered as its water solubility.

Figure 4:
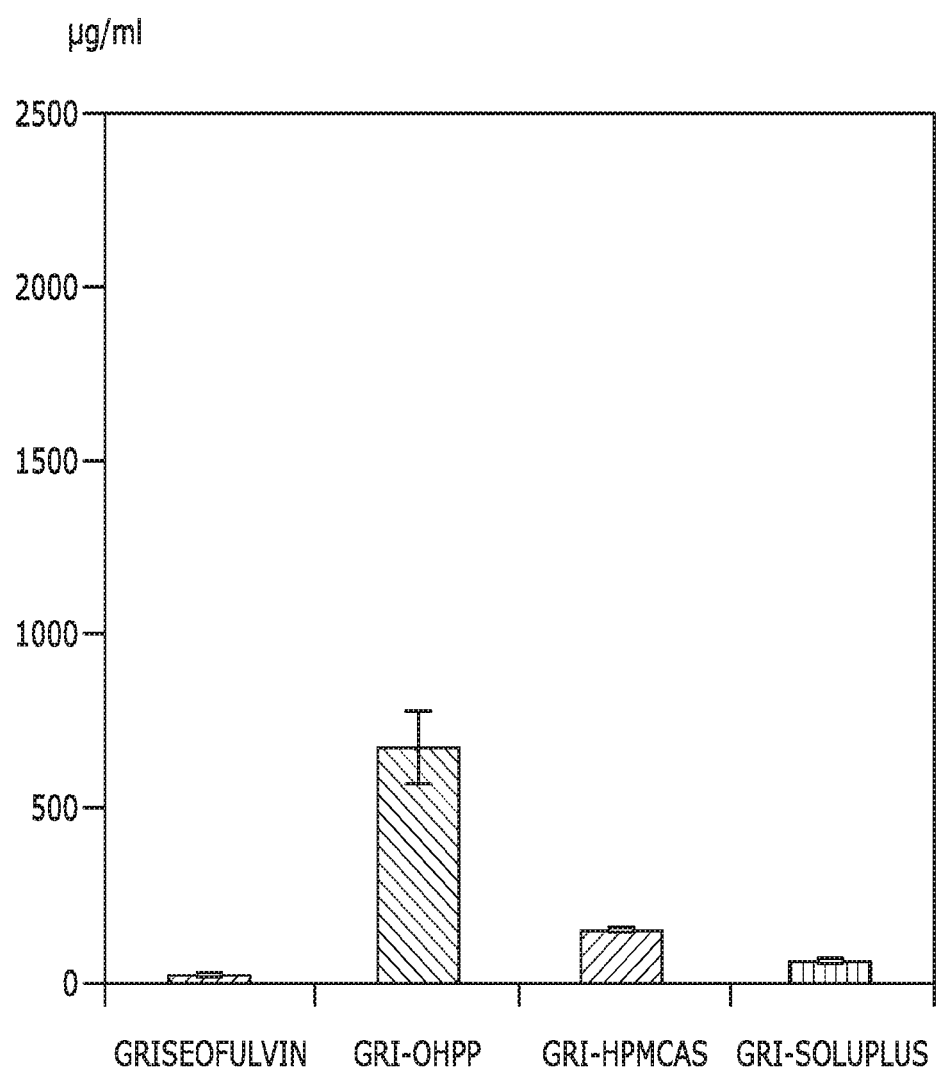
FIG. 4 provides a graph showing the solubility of griseofulvin when incorporated with OHPP, HPMCAS, and Soluplus, as compared with that of griseofulvin alone. The ratio between griseofulvin and excipient was 1/3, with total dispersed griseofulvin of 2,500 µg/mL in HBSS buffer (37° C.). The mixing time was 2 h before subjecting the dispersion to centrifugation to collect supernatant for griseofulvin quantification.

The water solubility of griseofulvin for griseofulvin alone, Gri-OHPP, Gri-HPMCAS, and Gri-Soluplus are compared in FIG. 4. The solubility of griseofulvin was around 784.7 µL/mL with Gri-OHPP, much greater than that of griseofulvin alone (around 17.5 µL/mL), Gri-HPMCAS (around 124.4 µL/mL), and Gri-Soluplus (around 68.2 µL/mL).

Example 6-5: Solubility of Docetaxel, with API/Excipient Ratio of 1/3

One part of docetaxel was physically incorporated with 3 parts of OHPP, and the final product was in solid form. The combined material between docetaxel and OHPP is termed as "docetaxel-OHPP complex", "Doc-OHPP complex", or "Doc-OHPP" in this document. Similarly the physically combined material between docetaxel and HPMCAS is termed as "docetaxel-HPMCAS complex", "Doc-HPMCAS complex", or "Doc-HPMCAS"; the physically combined material between docetaxel and Soluplus is termed as "docetaxel-Soluplus complex", "Doc-Soluplus complex", or "Doc-Soluplus".

To evaluate the solubility of docetaxel in aqueous system, 10 mg of each complex or 2.5 mg docetaxel alone was mixed with 1.0 mL Hank's Balanced Salt Solution (HBSS) under constant vortex for 10 min at 20° C. Thereafter, the dispersions were centrifuged at 16,000 g for 10 min, and the supernatants were collected for docetaxel quantification using HPLC. The concentration of docetaxel in the supernatant was considered as its water solubility.

Figure 5:
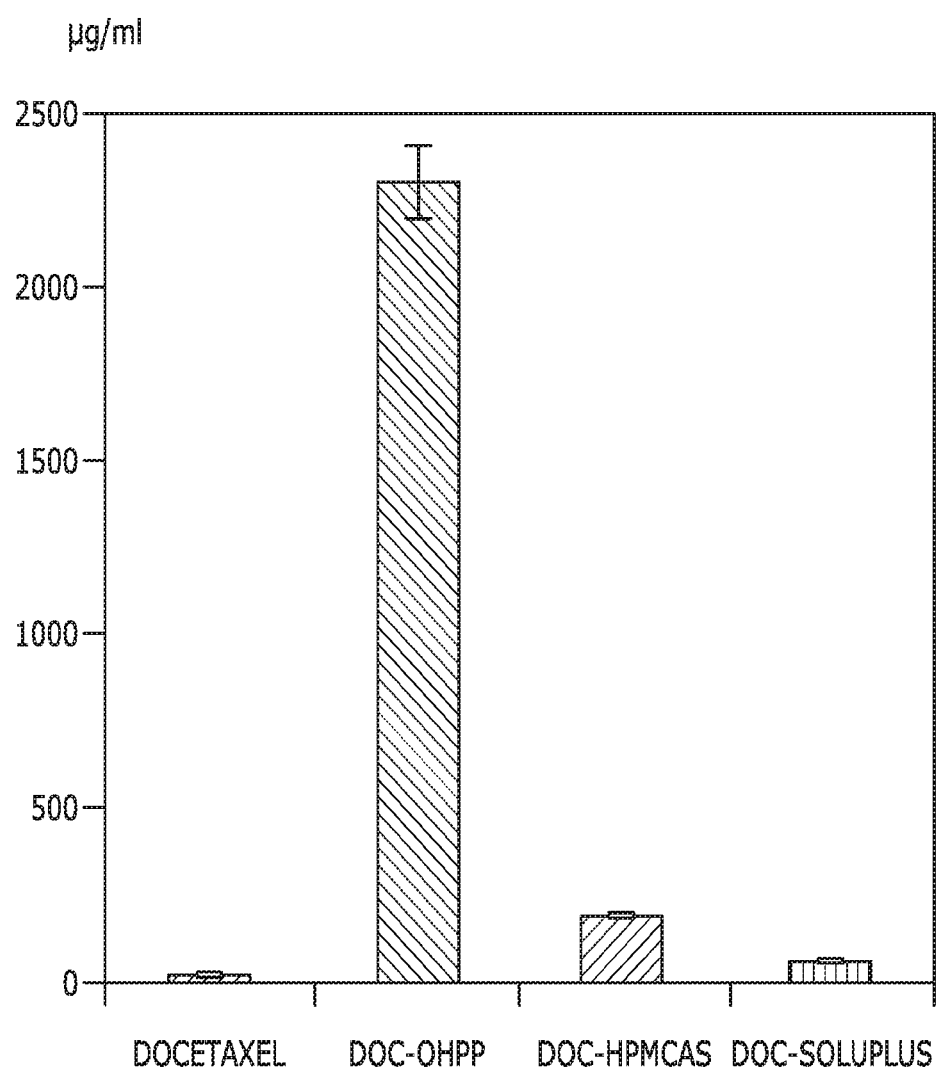
FIG. 5 provides a graph showing the solubility of docetaxel when incorporated with OHPP, HPMCAS, and Soluplus, as compared with that of docetaxel alone. The ratio between docetaxel and excipient was 1/3, with total dispersed docetaxel of 2,500 µg/mL in HBSS buffer (20° C.). The mixing time was 10 min before subjecting the dispersion to centrifugation to collect supernatant for docetaxel quantification.

The water solubility of docetaxel for docetaxel alone, Doc-OHPP, Doc-HPMCAS, and Doc-Soluplus are compared in FIG. 5. The solubility of docetaxel was around 2,347 µL/mL with Doc-OHPP, much greater than that of docetaxel alone (around 11.1 µL/mL), Doc-HPMCAS (around 215.9 µL/mL), and Doc-Soluplus (around 55.7 µL/mL).

Example 6-6: Solubility of Itraconazole, with API/Excipient Ratio of 1/3

One part of itraconazole was physically incorporated with 3 parts of OHPP, and the final product was in solid form. The combined material between itraconazole and OHPP is termed as "itraconazole-OHPP complex", "Itr-OHPP complex", or "Itr-OHPP" in this document. Similarly the physically combined material between itraconazole and HPMCAS is termed as "itraconazole-HPMCAS complex", "Itr-HPMCAS complex", or "Itr-HPMCAS"; the physically combined material between itraconazole and Soluplus is termed as "itraconazole-Soluplus complex", "Itr-Soluplus complex", or "Itr-Soluplus".

To evaluate the solubility of itraconazole in aqueous system, 10 mg of each complex or 2.5 mg itraconazole alone was mixed with 1.0 mL Hank's Balanced Salt Solution (HBSS) under constant vortex for 10 min at 20° C. Thereafter, the dispersions were centrifuged at 16,000 g for 10 min, and the supernatants were collected for itraconazole quantification using HPLC. The concentration of itraconazole in the supernatant was considered as its water solubility.

Figure 6:
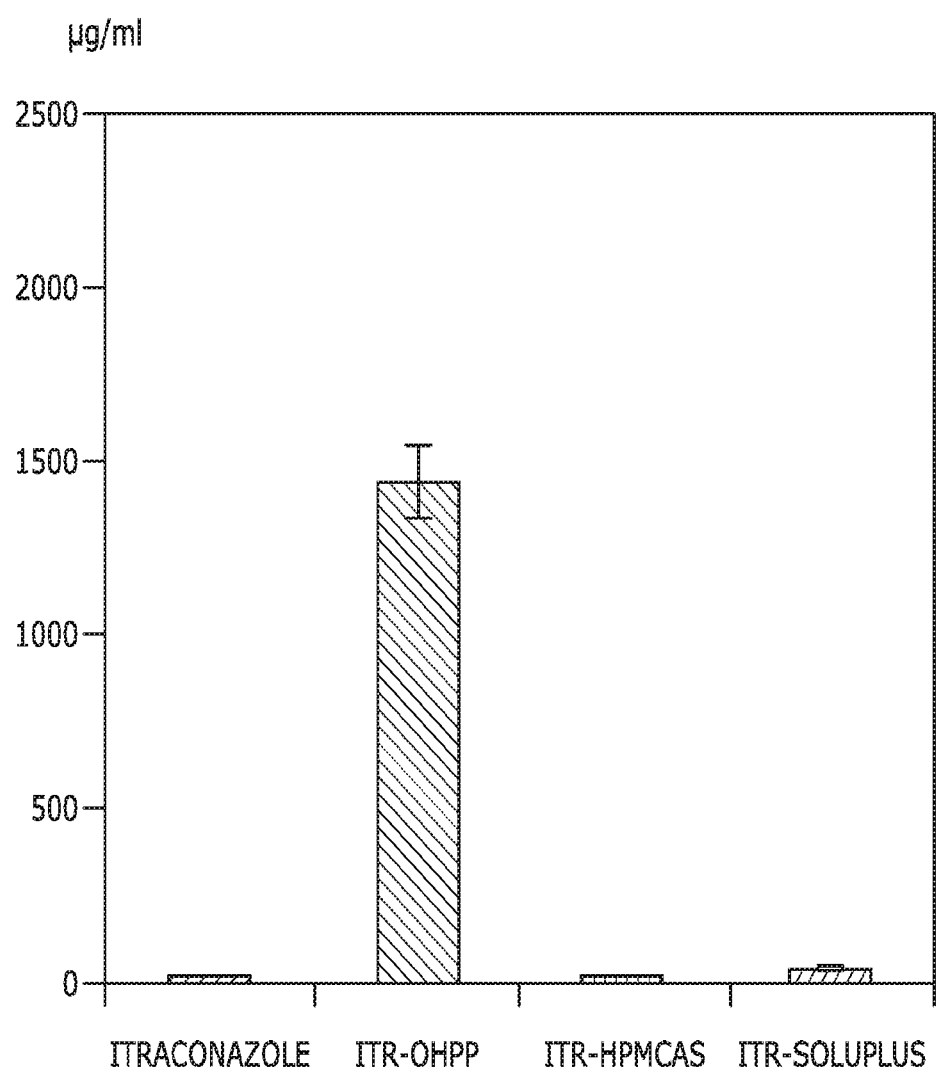
FIG. 6 provides a graph showing the solubility of itraconazole when incorporated with OHPP, HPMCAS, and Soluplus, as compared with that of itraconazole alone. The ratio between itraconazole and excipient was 1/3, with total dispersed itraconazole of 2,500 µg/mL in HBSS buffer (20° C.). The mixing time was 10 min before subjecting the dispersion to centrifugation to collect supernatant for itraconazole quantification.

The water solubility of itraconazole for itraconazole alone, Itr-OHPP, Itr-HPMCAS, and Itr-Soluplus are compared in FIG. 6. The solubility of itraconazole was around 1,439.9 µL/mL with Itr-OHPP, much greater than that of itraconazole alone (around 0.96 µL/mL), Itr-HPMCAS (around 4.6 µL/mL), and Itr-Soluplus (around 35.7 µL/mL).

Example 6-7: Solubility of Curcumin, with API/Excipient Ratio of 1/9

One part of curcumin was physically incorporated with 9 parts of OHPP, and the final product was in solid form. The combined material between curcumin and OHPP is termed as "curcumin-OHPP complex", "Cur-OHPP complex", or "Cur-OHPP" in this document. Similarly the physically combined material between curcumin and HPMCAS is termed as "curcumin-HPMCAS complex", "Cur-HPMCAS complex", or "Cur-HPMCAS"; the physically combined material between curcumin and Soluplus is termed as "curcumin-Soluplus complex", "Cur-Soluplus complex", or "Cur-Soluplus".

To evaluate the solubility of curcumin in aqueous system, 10 mg of each complex or 1.0 mg curcumin alone was mixed with 1.0 mL Hank's Balanced Salt Solution (HBSS) under constant agitation for 2 h in a shaking water bath (37° C., 100 rpm). Thereafter, the dispersions were centrifuged at 16,000 g for 10 min, and the supernatants were collected for curcumin quantification using HPLC. The concentration of curcumin in the supernatant was considered as its water solubility.

Figure 7:
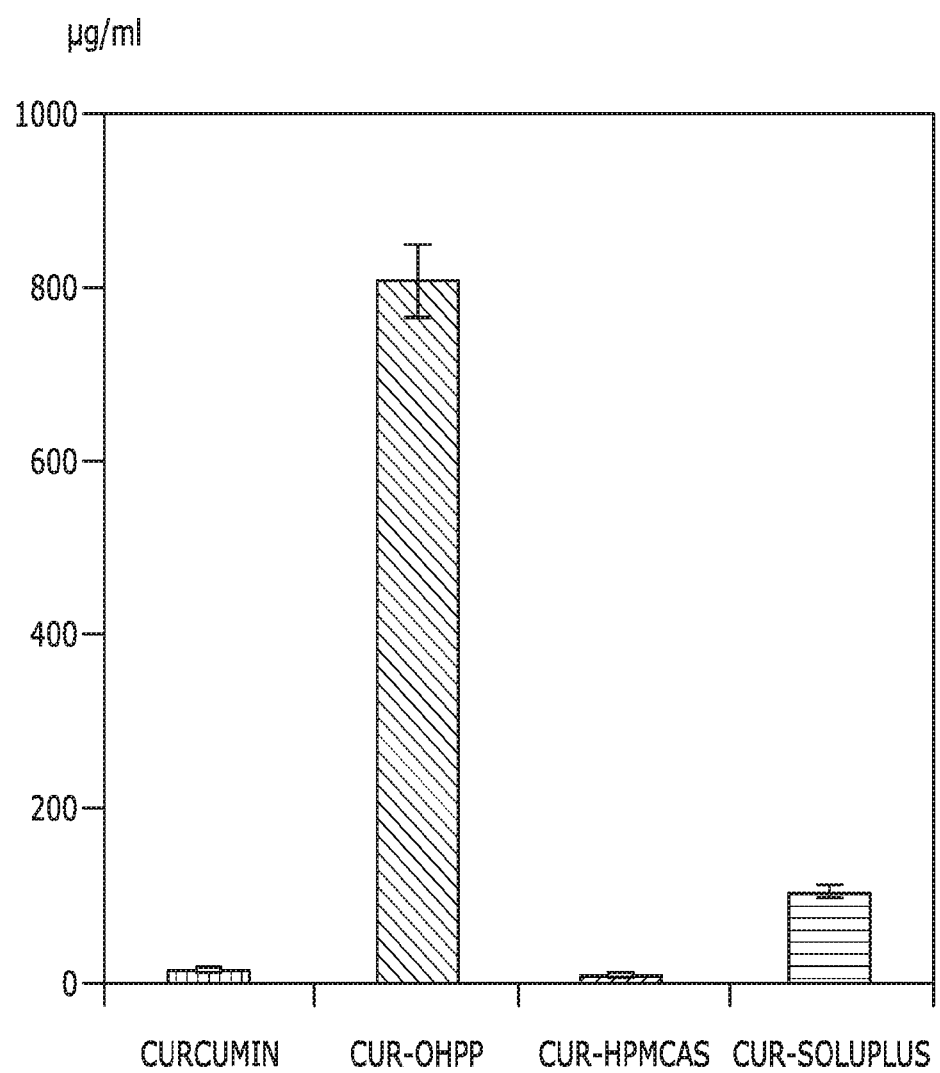
FIG. 7 provides a graph showing the solubility of curcumin when incorporated with OHPP, HPMCAS, and Soluplus, as compared with that of curcumin alone. The ratio between curcumin and excipient was 1/9, with total dispersed curcumin of 1,000 µg/mL in HBSS buffer (37° C.). The mixing time was 2 h before subjecting the dispersion to centrifugation to collect supernatant for curcumin quantification.

The water solubility of curcumin for curcumin alone, Cur-OHPP, Cur-HPMCAS, and Cur-Soluplus are compared in FIG. 7. The solubility of curcumin was around 862.5 µL/mL with Cur-OHPP, much greater than that of curcumin alone (around 7.2 µL/mL), Cur-HPMCAS (around 5.0 µL/mL), and Cur-Soluplus (around 85.4 µL/mL).

Example 6-8: Solubility of Celecoxib, with API/Excipient Ratio of 1/5

One part of celecoxib was physically incorporated with 3 parts of OHPP and 2 parts of HPMCAS, and the final product was in solid form. The combined material among celecoxib and OHPP and HPMCAS is termed as "celecoxib-OHPP-HPMCAS complex", "Cel-OHPP-HPMCAS complex", or "Cel-OHPP-HPMCAS" in this document. Similarly the physically combined material between celecoxib and HPMCAS is termed as "celecoxib-HPMCAS complex", "Cel-HPMCAS complex", or "Cel-HPMCAS"; the physically combined material between celecoxib and Soluplus is termed as "celecoxib-Soluplus complex", "Cel-Soluplus complex", or "Cel-Soluplus".

To evaluate the solubility of celecoxib in aqueous system, 6 mg of each complex or 1.0 mg celecoxib alone was mixed with 1.0 mL Hank's Balanced Salt Solution (HBSS) under constant agitation for 2 h in a shaking water bath (37° C., 100 rpm). Thereafter, the dispersions were centrifuged at 16,000 g for 10 min, and the supernatants were collected for celecoxib quantification using HPLC. The concentration of celecoxib in the supernatant was considered as its water solubility.

Figure 8:
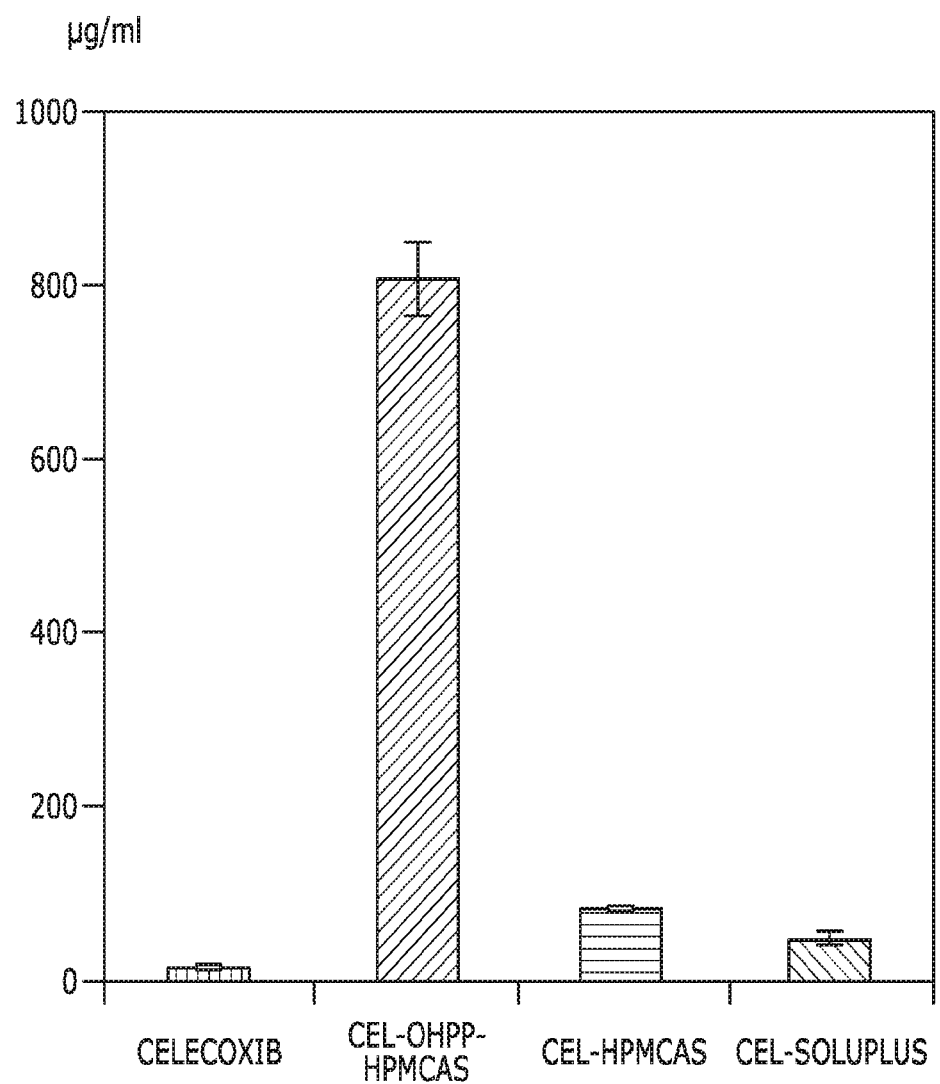
FIG. 8 provides a graph showing the solubility of celecoxib when incorporated with OHPP, HPMCAS, and Soluplus, as compared with that of celecoxib alone. The ratios between celecoxib and each excipient was 1/5, with total dispersed API of 1,000 µg/mL in HBSS buffer (37° C.). The mixing time was 2 h before subjecting the dispersion to centrifugation to collect supernatant for celecoxib quantification. The weight ratio of celecoxib, OHPP, and HPMCAS was 1, 3, and 2 respectively for the Cel-OHPP-HPMCAS preparation.

The water solubility of celecoxib for celecoxib alone, Cel-OHPP-HPMCAS, Cel-HPMCAS, and Cel-Soluplus are compared in FIG. 8. The solubility of celecoxib was around 772.3 µL/mL with Cel-OHPP-HPMCAS, much greater than that of celecoxib alone (around 12.8 µL/mL), Cel-HPMCAS (around 62.9 µL/mL), and Cel-Soluplus (around 40.3 µL/mL).

Example 7: Degree of Substitution (DS) of OHPP

DS of OHHP determined using $^1$H NMR

OHPP was hydrolyzed sequentially in alkaline and acidic conditions. First, 0.5 g OHPP and 0.1 g NaOH were dissolved in 5 mL deionized $H_2O$ and heated in a boiling-water bath for 1 h. Thereafter, 0.25 mL 5M $H_2SO_4$ were added to the OHPP dispersion to neutralize the fluid. For acidic hydrolyzation, 5M $H_2SO4$ was added to the neutralized system to bring the concentration of $H^+$ to 1N, and the reactant was heated in a boiling-water bath for 1 h. Thereafter, the system was neutralized using 5M NaOH. The product solution was lyophilized to collect hydrolyzed OHPP.

Twenty milligrams of hydrolyzed OHHP solid was dissolved in 1 mL deuterium oxide ($D_2O$) and lyophilized again. The $D_2O$-exchanged OHHP was dissolved in 1 mL $D_2O$ for NMR determination of DS for both hydroxypropyl group and octenylsuccinate group with OHHP.

The $^1$H NMR measurements were performed at 50° C. with a Bruker Avance DRX-500 NMR spectrometer operating at 499.89 MHz and equipped with a 5 mm inverse-detection triple-resonance Z-gradient probe.

Figure 9:
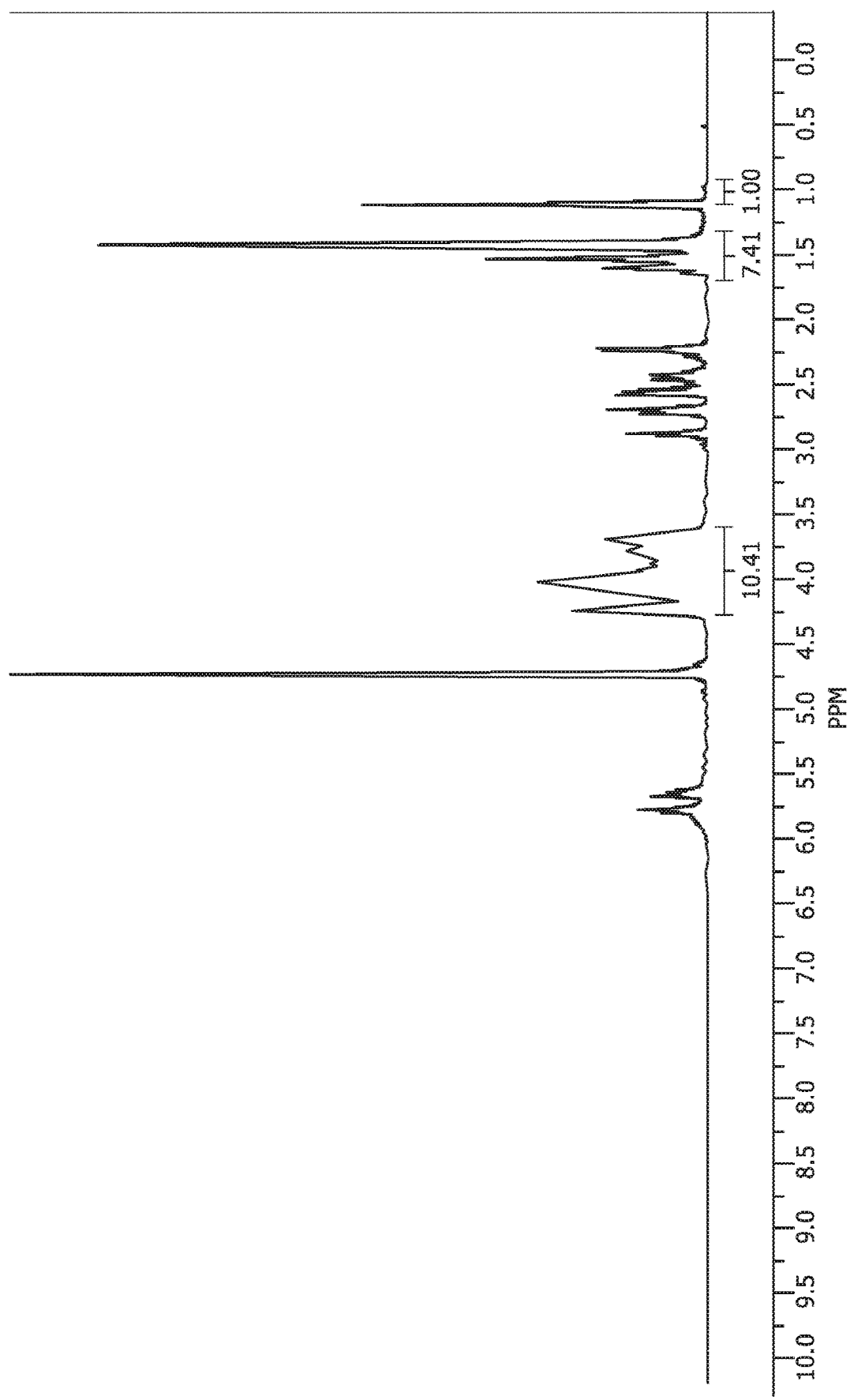
FIG. 9 provides an image of the $^1$H NMR spectra of hydrolyzed octenylsuccinate hydroxypropyl phytoglycogen (OHPP).

According to the $^1$H NMR spectra (FIG. 9), the relative molar amount of octenyl succinate calculated from the signal peak area (around 1.1 ppm) of its methyl group (—$CH_3$) was 0.33.

The relative molar amount of hydroxypropyl group was obtained from the signal peak area of its methyl group. This was calculated by subtracting the signal peak area related to some methylene (—$CH_2$—) units in the octenyl succinate group from the signal peak area ranging 1.34-1.64 ppm. The relative molar amount of hydroxypropyl group thus calculated was 1.8.

The relative molar amount of glucosyl unit of phytoglycogen was obtained from the signal peak area associated with C2, C3, C4, C5, and C6 of glucosyl units. This was calculated by subtracting the signal peak area of —O—$CH_2$— and —CH($CH_3$)—O— of the hydroxypropyl group from the signal peak area ranging 3.57-4.35 ppm. The relative molar amount of glucosyl unit thus calculated was 0.83.

Therefore, the DS of octenyl succinate group was 0.33/0.83=0.40, and the DS of hydroxypropyl group was 1.8/0.83=2.17.

Example 8: Caco-2 Monolayer Permeation of Niclosamide and Celecoxib

Caco-2 cells were seeded in the inserts with tissue-culture-treated polyester membranes (Transwells, 0.4 µm pore size, Corning) at a density of $1\times10^4$ cells/well. After seeding, the medium was changed every other day until the day of the permeation test. All tests were performed on day 21 after seeding. For the test, the culture medium was removed and the cells were washed twice with PBS buffer. The cells were then equilibrated in HBSS for 15 min prior to each study, and then apical and basolateral solution were aspirated.

To measure the apical-to-basolateral permeation of API, 0.5 mL of each test solution was added to the apical compartment, and the basolateral compartment received 1.5 mL HBSS. As a control, reference cells were incubated with 0.5 mL blank HBSS on the apical side, while the basolateral side received 1.5 mL of HBSS. All cultures were incubated in an incubator (5% $CO_2$, 37° C.) for 2 h. After the incubation, the apical and the basolateral solutions were collected respectively and their amounts of API were determined using HPLC.

The loaded dispersions were prepared in two steps: (1) dispersing API-excipient complex solid and API alone in HBSS at the doses of 1000 µg/mL or 100 µg/mL, and (2)

subjecting each dispersion to centrifugation (16,000 g, 5 min) to collect supernatant. The supernatants were loaded in the apical compartments of inserts.

Figure 10:
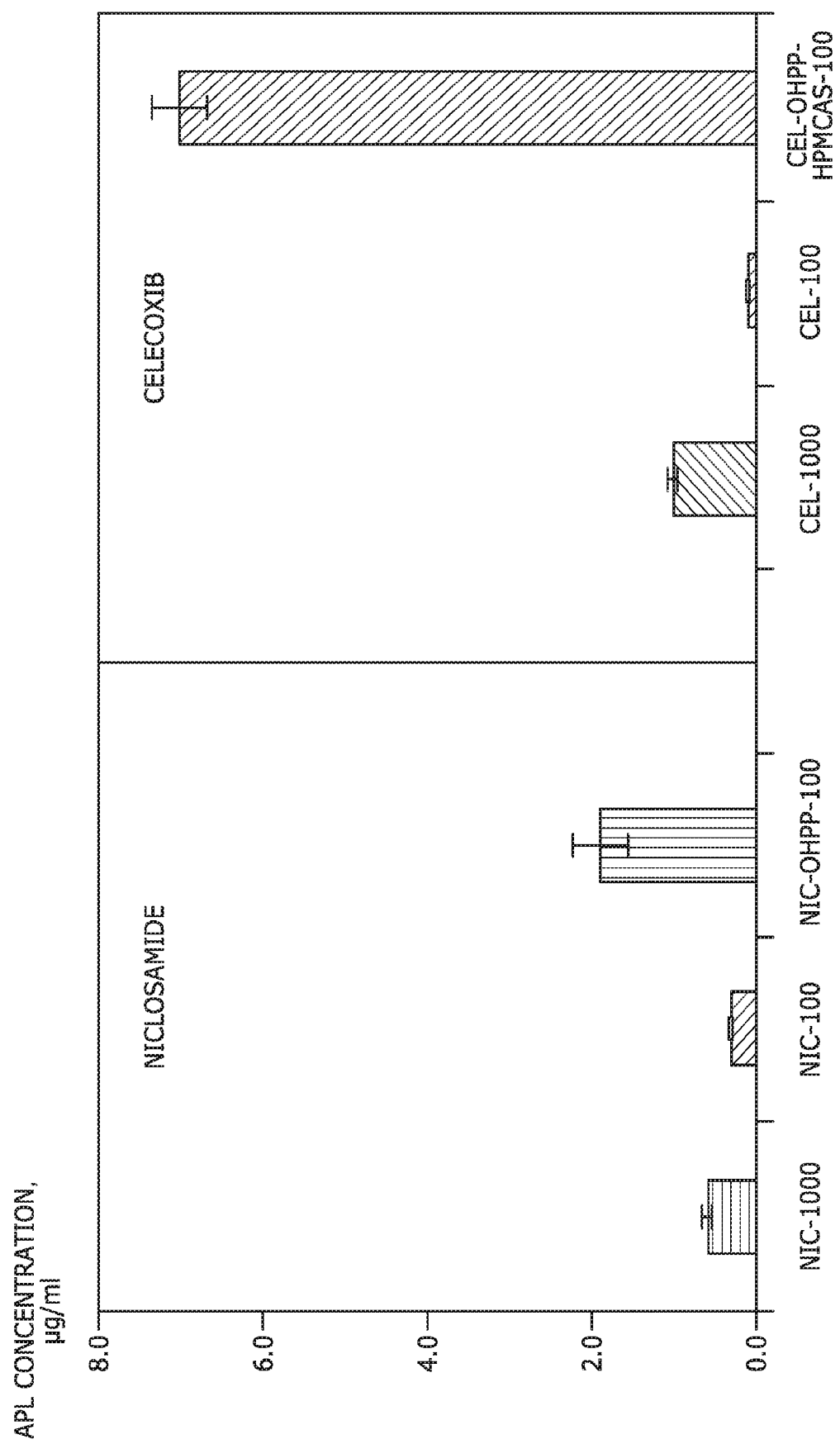
FIG. 10 provides a graph showing the concentration of APIs in the basolateral compartment of Caco-2 cell monolayer as affected by the use of OHPP. Nic-1000 and Nic-100.

FIG. 10 shows the impact of improved API solubility on its permeation through epithelial membranes, using Caco-2 monolayer as the model. For niclosamide alone and celecoxib alone, the soluble portion of API in the simulated intestinal buffer (HBSS) was not sufficient to provide an appreciable permeation, even at a very high initial dose (1,000 µg/mL). When OHPP was used, the permeation was substantially increased even at a low initial concentration (100 µg/mL). Evidently, OHPP greatly enhanced the permeation of API molecules.

Example 9: In Vitro Anticancer Efficacies of Niclosamide and Paclitaxel Enhanced by OHPP Paclitaxel is an anticancer drug with activity against a wide variety of human malignancies, such as ovarian, breast and lung, bladder, prostate, melanoma and esophageal cancer. However, its poor water-solubility limits its effective application. Commercially, paclitaxel is solubilized in cremophor EL and ethanol for intravenous administration, which may cause allergic reactions and precipitation on aqueous dilution. Recently, paclitaxel has been used in the clinical trials for gastric cancers and other advanced solid cancer via oral administration.

Niclosamide is an anthelmintic drug used for the treatment of worm infestations in humans and animals. Importantly, recent studies have shown that niclosamide is a promising anticancer agent against various human cancers, such as leukemia, ovarian and breast carcinoma, which results from its ability in interfering with multiple cell signaling/regulatory pathways, such as NF-κB, ROS, Notch, Wnt/b-catenin and mTORc1. These properties assure niclosamide less tendency to cause resistance from cancer cells. As a highly permeable drug, however, niclosamide's low water solubility greatly reduces its efficacy.

For the oral administration of poorly water-soluble anticancer APIs such as paclitaxel, niclosamide, and docetaxel, sufficient water solubility is essential to their high local bioaccessibility to cancer cells in the gastrointestinal tract and to their bioavailability for reaching cancer cells at locations other than the GI tract. While OHPP is able to dissolve paclitaxel and niclosamide, we wanted to confirm that the dissolved APIs were accessible to cancer cells and show cytotoxicity. To evaluate the performance of OHPP to solubilize and release APIs, we tested the cytotoxicity of paclitaxel and niclosamide complexed with OHPP.

In drug screening and in vitro efficacy studies, dimethyl sulfoxide (DMSO) has been used to dissolve poorly water-soluble APIs. While DMSO cannot be used in actual drug formulations, the DMSO-dissolved API can be used as a benchmark to evaluate the efficacies of APIs dissolved by OHPP and other commercial solubilizers, such as HPMCAS and Soluplus. As shown in FIG. 11, the efficacies of excipient-dispersed paclitaxel and niclosamide were tested against HeLa (a cervical cancer cell line, ATCC®CCL-2™) and PC-3 (a prostate cancer cell, ATCC®CRL-1435™) respectively.

The in vitro anticancer testing results were highly encouraging. As shown in FIG. 11A, OHPP-dispersed paclitaxel (Pac-OHPP) demonstrated at least an equivalent, if not higher anti-HeLa efficacy as compared with DMOS-dissolved preparation (Pac-DMSO). In particular, the cytotoxicity of Pac-OHPP was significantly higher than that of Pac-DMSO at concentrations below 1.0 µg/mL. Based on the plot of cell viability vs. dose, $IC_{50}$ was approximately 0.095 µg/mL for Pac-OHPP, and 0.19 µg/mL for Pac-DMSO. In comparison, $IC_{50}$ for Pac-HPMCAS and Pac-Soluplus were 1.74 and 9.8 µg/mL, respectively.

For niclosamide against PC-3 cell, as shown in FIG. 11B, OHPP-dispersed niclosamide (Nic-OHPP) demonstrated a similar anti-tumoral efficacy as compared with DMSO-dissolved preparation (Nic-DMSO). Based on the plot of cell viability vs. dose, $IC_{50}$ was approximately 0.18 µg/mL for Nic-OHPP, and 0.15 µg/mL for Nic-DMSO. In comparison, the $IC_{50}$ for Pac-HPMCAS and Pac-Soluplus were 2.1 and 2.3 µg/mL, respectively.

It should be noted that, the X-axis and the $IC_{50}$ results for Pac (Nic)-DMSO, Pac (Nic)-OHPP, Pac (Nic)-HPMCAS, and Pac (Nic)-Soluplus were all "apparent dose", i.e. those calculated based on the total API amount in the initial stock dispersion and dilution factors. For Pac (Nic)-HPMCAS and Pac (Nic)-Soluplus, the majority of API added in buffer was not soluble in the initial preparations. Therefore, the actual amount of paclitaxel (niclosamide) in the soluble portion (that was sequentially diluted for cytotoxicity testing) was much lower than that for Pac (Nic)-DMSO and Pac (Nic)-OHPP. This procedure of diluting the dissolved portion of API stock simulates the scenario in which the therapeutic outcome of a dosage form is governed by the dissolved API portion that may reach the target sites.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of making an aqueous composition of an active pharmaceutical ingredient (API) and a solubilizing agent, comprising the steps of:
   a) providing a highly branched carbohydrate polymer;
   b) activating the highly branched carbohydrate polymer using a basic solution;
   c) reacting the activated highly branched carbohydrate polymer with a polyalkylene glycol or alkylene oxide to form a modified highly branched carbohydrate polymer;
   d) adding to the modified highly branched carbohydrate polymer with a hydrophobic or amphiphilic group to yield said solubilizing agent; and
   e) combining said solubilizing agent with API, wherein the hydrophobic or amphiphilic group of step d) comprises octenyl succinate group.

2. The method of claim 1, wherein the alkylene oxide is used.

3. A method of making an aqueous composition of an active pharmaceutical ingredient (API), comprising mixing the solubilizing agent of claim 1 with a hydrophobic solute compound as the API.

4. The method of claim 1, wherein the alkylene oxide of step c) is ethylene oxide or propylene oxide.

5. The method of claim 1, wherein the polyalkylene glycol of step c) is polyethylene glycol or polypropylene glycol.

6. The method of claim 1, wherein the hydrophobic or amphiphilic group of step d) further comprises an acetate group, a propionate group, a butyrate group, or a combination thereof.

7. The method of claim 3, wherein the hydrophobic solute compound is mixed with the solubilizing agent using a method selected from the group consisting of extrusion, mixing, spray drying, vacuum drying, kneading, rolling, ultra-sonication, vibration, and milling.

* * * * *